United States Patent
Tada et al.

(10) Patent No.: US 9,101,418 B2
(45) Date of Patent: Aug. 11, 2015

(54) MEDICAL DEVICE AND VASCULARIZATION METHOD

(75) Inventors: Yuichi Tada, Kanagawa (JP); Yuji Nakagawa, Kanagawa (JP); Suguru Hata, Kanagawa (JP); Yasushi Kinoshita, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 344 days.

(21) Appl. No.: 13/406,853

(22) Filed: Feb. 28, 2012

(65) Prior Publication Data
US 2012/0221009 A1    Aug. 30, 2012

(30) Foreign Application Priority Data
Feb. 28, 2011    (JP) .................................. 2011-042756

(51) Int. Cl.
| | |
|---|---|
| *A61B 17/88* | (2006.01) |
| *A61M 25/10* | (2013.01) |
| *A61B 17/72* | (2006.01) |
| *A61B 17/74* | (2006.01) |
| *A61B 17/34* | (2006.01) |
| *A61B 17/84* | (2006.01) |
| *A61B 17/56* | (2006.01) |

(52) U.S. Cl.
CPC ........... *A61B 17/7258* (2013.01); *A61B 17/742* (2013.01); *A61B 17/3472* (2013.01); *A61B 17/848* (2013.01); *A61B 17/8811* (2013.01); *A61B 2017/561* (2013.01); *A61M 25/10* (2013.01)

(58) Field of Classification Search
CPC ........................... A61M 25/10; A61B 17/8811
USPC ............. 604/90, 104, 131, 506, 96.01, 97.01, 604/158, 164.03, 164.06; 606/93, 95, 92, 606/94
See application file for complete search history.

(56) References Cited

U.S. PATENT DOCUMENTS

| | | | | |
|---|---|---|---|---|
| 3,598,119 | A | * | 8/1971 | White ............................ 604/506 |
| 3,861,396 | A | * | 1/1975 | Vaillancourt et al. .......... 604/129 |
| 5,667,489 | A | * | 9/1997 | Kraff et al. ....................... 604/22 |
| 2011/0125132 | A1 | * | 5/2011 | Krolik et al. ................... 604/509 |

FOREIGN PATENT DOCUMENTS

| | | |
|---|---|---|
| JP | 11-137566 A | 5/1999 |
| JP | 2009-207710 A | 9/2009 |

* cited by examiner

*Primary Examiner* — David Bates
(74) *Attorney, Agent, or Firm* — Buchanan Ingersoll & Rooney PC

(57) ABSTRACT

A medical device includes a tubular body having a first lumen so designed as to receive a fluid from an opening at one end of the first lumen and discharge the fluid from an opening at the other end of the first lumen, and an expandable body attached to the tubular body. The first lumen communicates with the space inside the expandable body and the expandable body expands by the internal pressure of the fluid which is injected from the opening at one end and enters the space inside the expandable body through the first lumen.

9 Claims, 21 Drawing Sheets

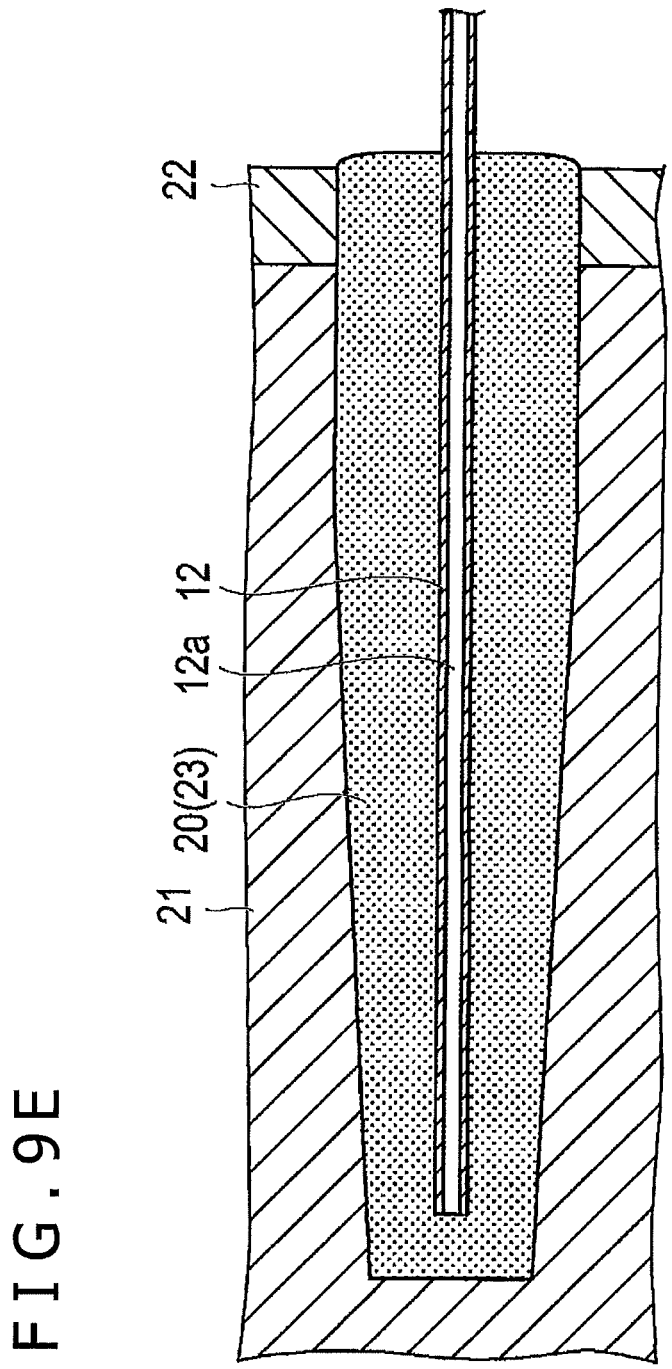

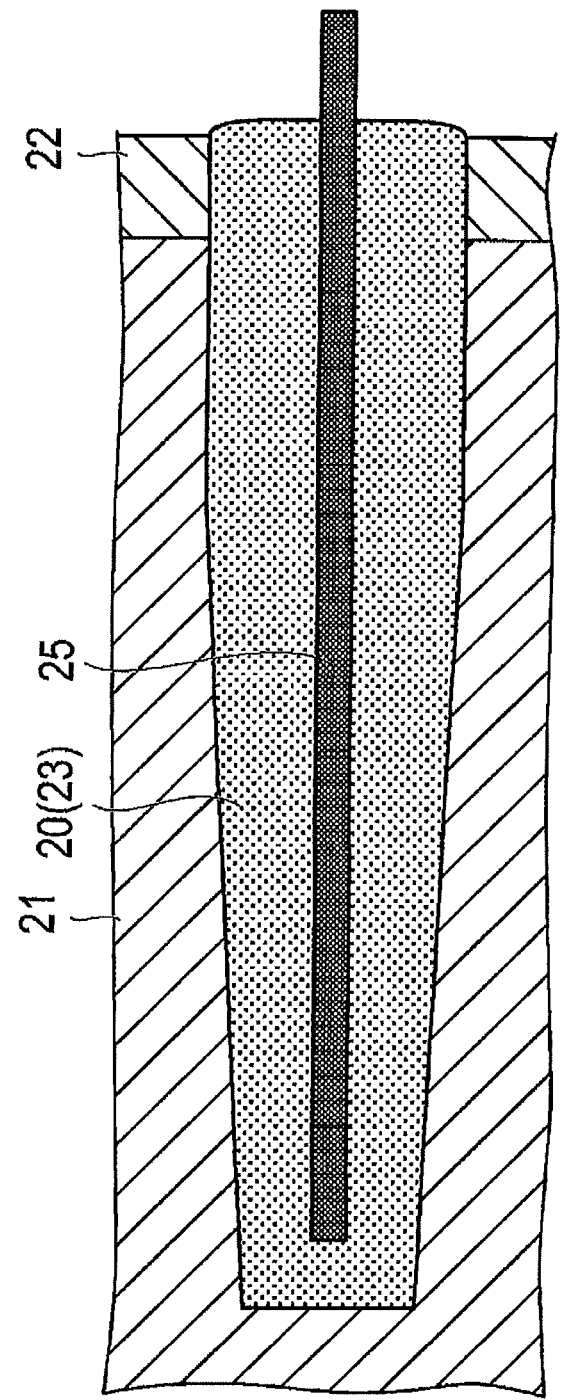

MEDICAL DEVICE AND VASCULARIZATION METHOD

FIELD OF THE INVENTION

The present invention relates to a medical device to inject a fluid into a hole made in the living tissue such as bone and muscle, and a method for vascularization in a hole in a bone.

BACKGROUND DISCUSSION

The fracture that occurs most frequently without respect to age is the femoral fracture. Reportedly, 150,000 persons suffer from femoral fracture every year in Japan. This is a serious social problem because aged persons tend to need nursing care once they suffer from femoral fracture.

Known methods for curing femoral fracture include replacement of the bone head with an artificial bone head, bonding the fractured parts with an implant, and conservative treatment. The second method (osteosynthesis) is preferred because it employs the patient's own tissue and is minimally invasive. Osteosynthesis in this case is accomplished by internally fixing the femur.

The implant (such as nail, screw, and pin) used for osteosynthesis of the femur is usually designed such that it is arranged in the lengthwise direction of the neck of the femur to stabilize the fractured part. An example of the implant for femoral osteosynthesis is a lag screw screwed into the bone head across the fracture plane in the neck of the femur, as disclosed in Japanese Patent Laid-Open Nos. Hei 11-137566 and 2009-207710.

When the screw type implant is used to fix the fractured part, it is common practice to previously insert a Kirschner wire into the neck of the femur in order to prevent the fractured part from being turned by the torque around the axis along the lengthwise direction of the neck of the femur which is produced as the lag screw is screwed in. The Kirschner wire (called "K wire" for short hereinafter) is arranged to penetrate the cartilage which is called epiphysis line, existing in the bone head. The K wire helps the screw type implant advance to the desired position, and it is then withdrawn after the implant has been screwed into the bone.

Osteosynthesis for femoral fracture with an implant has the possibility of causing ischemic disorder such as bone head necrosis and LSC (Late Segmental Collapse) if the fracture involves the breakage of blood vessels (especially the inside and outside femoral circumflex arteries) which supply blood to the bone head. Unfortunately, there is not any established procedure for preventing and curing such ischemic disorder despite a strong desire.

SUMMARY

The medial device disclosed here is configured to inject a fluid into a hole to which the medical device is securely fixed. The medical device includes a tubular body having a first lumen so designed as to receive a fluid from an opening at one end of the lumen and discharge the fluid from an opening at the other end of the lumen, and an expandable body attached to the tubular body, wherein the first lumen communicates with the space inside the expandable body and the expandable body expands by the internal pressure of the fluid which is injected from the opening at one end and enters the space inside the expandable body through the first lumen. The medical device is thus able to be securely fixed to a hole as the expandable body expands by virtue of the fluid flowing into the expandable body from the lumen. In other words, the medical device can be securely fixed to a hole by injection of a fluid into the lumen so that the medical device remains securely fixed during fluid injection.

The medical device can also include a second tubular body having a second lumen which is arranged inside and coaxially with the first lumen. The medical device is thus configured to include a first flow (in tubular shape) of fluid injected into a first tubular body and a second flow (in rod-like shape) of fluid injected into a second tubular body.

The tubular body preferably possesses a tapering shape such that the first lumen decreases in inside diameter from the opening at one end to the opening at the other end. The tapering shape causes the fluid to experience more resistance as the fluid approaches the far end, which helps the fluid injected into a first lumen to flow more easily into the expandable body.

The medical device is preferably constructed to be arranged in a hole and fixed to the hole as the expandable body expands and comes into close contact with the inside wall of the hole. The medical device can thus be used in a context allowing the medical device to be securely fixed to the hole owing to the expandable body which expands by the fluid injected from the lumen. The medical device can thus be securely fixed to the hole by injecting fluid into the lumen so that the medical device remains securely fixed during fluid injection.

The expandable body can be configured to define a gas discharge channel between the expandable body of the medical device fixed to the hole and the inside wall of the hole. It is thus possible to feed the fluid into a hole and discharge gas from the hole simultaneously.

The tubular body can be provided with surface treatment on its outer surface to prevent the adhesion of fluid. This allows the medical device to be more easily removed from the hole into which the fluid has been injected.

According to another aspect, a medical device positionable in a hole in a bone of a human body comprises: a tubular body possessing a size and configuration permitting the tubular body to be positioned in a hole in a bone of a human body; a lumen extending through the tubular body, and an expandable body fixed to the tubular body. The lumen possesses an opening at one end of the lumen permitting a liquid to be introduced into the lumen and also possesses an opening at an opposite end of the lumen permitting the liquid in the lumen to be discharged from the lumen and into the hole in the bone. The expandable body surrounds an interior space in fluid communication with the lumen in the tubular body so that the liquid in the lumen of the tubular body flows into the interior space of the expandable body and outwardly expands the expandable body to cause the expandable body to contact an inner surface of the bone surrounding the hole to fix the medical device in position in the hole in the bone. The lumen possesses a size which gradually decreases at least from the expandable body toward the opening at the opposite end of the lumen so that the liquid introduced into the lumen by way of the opening at the one end of the lumen and flowing toward the opening at the opposite end of the lumen enters the interior space of the expandable body and outwardly expands the expandable body into contact with the inner surface of the bone surrounding the hole.

According to another aspect of the disclosure here, a method for vascularization in a hole in a bone involves introducing a vascularizing agent into a hole formed in a bone of a living body, and introducing a gel into the hole formed in the bone of the living body so that the gel forms a barrier on an inner surface of the hole in the bone hole. The gel is different from the vascularizing agent, and the vascularizing agent is surrounded by the gel.

Other features, characteristics and aspects of the medical device and method disclosed here will become more apparent from the following detailed description considered with reference to the accompanying drawings in which like reference numbers identify like features.

BRIEF DESCRIPTION OF THE DRAWINGS

FIG. 9E is a cross-sectional view showing one operational aspect of a method for curing ischemic disorder associated with femoral fracture using the medical device disclosed here.

FIG. 10E is a cross-sectional view showing an operational aspect of another method of using the medical device disclosed here for curing ischemic disorder associated with femoral fracture.

DETAILED DESCRIPTION

The following is a description of a first embodiment of the medical device disclosed here. Generally speaking, this first embodiment of the medical device includes a tubular body having a first lumen configured to receive a fluid (gel or liquid) from the opening at one end of the lumen and discharge the fluid from the opening at the other end of the lumen, and an expandable body attached to the tubular body, wherein the first lumen communicates with the space inside the expandable body and the expandable body expands by the internal pressure of the fluid which is injected from the opening at one end and enters the internal space of the expandable body through the first lumen.

Figure 1:
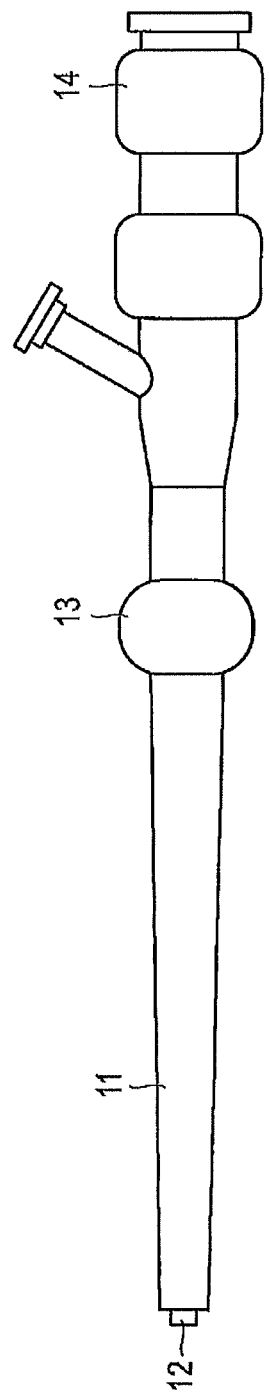
FIG. 1 is a side view of the medical device disclosed here according to one embodiment.
Figure 2:
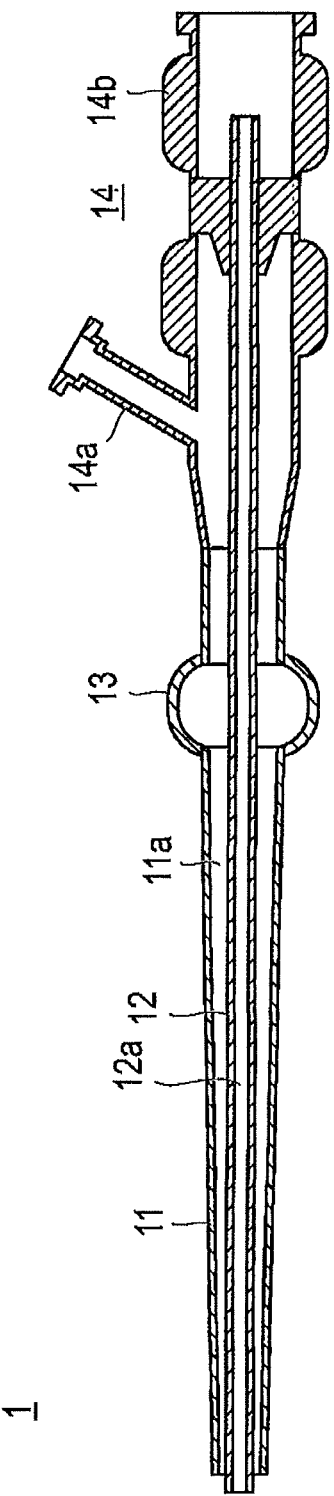
FIG. 2 is a longitudinal cross-sectional view of the medical device shown in FIG. 1.

As shown in FIGS. 1 and 2, the medical device 1 according to this first embodiment disclosed by way of example includes a first tubular body 11 having a first lumen 11a, a second tubular body 12 having a second lumen 12a and positioned coaxially in the first lumen 11a, an expandable body 13 arranged on the first tubular body 11, and a hub unit 14 which holds both the first tubular body 11 and the second tubular body 12. In other words, the medical device 1 according to the first embodiment has a double-tubular structure constructed of the first tubular body 11 having the first lumen 11a and the second tubular body 12 having the second lumen 12a.

The first tubular body 11 is a fluid transfer tube that permits a fluid injected from the opening at one end of the first tubular body 11 to be discharged from the opening at the other end of the tubular body 11 through the first lumen 11a. The first tubular body 11 may be formed from any material selected from known materials generally used in the field of medicine. A preferable material is one which is rigid enough to inhibit or prevent the tubular body from bending or breaking due to its own weight the weight of the fluid in the lumen. The following are typical examples of preferable materials for the first tubular body 11: polyolefins, such as polyethylene, polypropylene, ethylene-propylene copolymer, and ethylene-vinyl acetate copolymer, and their crosslinked or partially crosslinking products (e.g., crosslinked ethylene-vinyl acetate copolymer); resins, such as polyvinyl chloride, nylon elastomer, fluoroplastic, and polyurethane; rubbers, such as silicone rubber and latex rubber; and metallic materials, such as stainless steel, malleable stainless alloy, and shape-memory alloy (e.g., Ni Ti alloy). In the following description, one end of the tubular body for fluid injection is referred to as the "near end" (right end) and the other end of the tubular body for fluid discharge is referred to as the "far end" (left end).

The medical device disclosed here includes one tubular body (e.g., the first tubular body 11) as an essential component, and may also optionally include another tubular body (e.g., the second tubular body) having a lumen, with arranged inside and coaxially with the lumen in the one tubular body. The second tubular body 12 is a fluid transfer tube that permits the fluid injected from the opening at the near end to be discharged from the opening at the far end through the second lumen 12a. The second tubular body 12 may be formed from any material selected from known materials generally used in the field of medicine. A preferable material is one which is rigid enough to inhibit or prevent the tubular body from bending or breaking due to its own weight of or the weight of the fluid in the lumen. The following are typical examples of preferable materials for the second tubular body 12: polyolefins, such as polyethylene, polypropylene, ethylene-propylene copolymer, and ethylene-vinyl acetate copolymer, and their crosslinked or partially crosslinking products (e.g., crosslinked ethylene-vinyl acetate copolymer); resins, such as polyvinyl chloride, nylon elastomer, fluoroplastic, and polyurethane; rubbers, such as silicone rubber and latex rubber; and metallic materials, such as stainless steel, malleable stainless alloy, and shape-memory alloy (e.g., Ni Ti alloy). The first tubular body 11 and the second tubular body 12 may be formed from identical materials or different materials.

The expandable body 13 is a balloon configured to fix the medical device 1 to the hole formed in the living body by the K wire and in which the medical device 1 is placed. Specifically, the expandable body 13 expands in the direction perpendicular to the direction in which the medical device 1 extends as it receives the internal pressure of the fluid flowing through the internal space of the expandable body. After expansion, the outer surface of the expandable body 13 presses itself against the inner wall of the hole, thereby fixing the medical device 1 in place relative to the hole. The expandable body 13 may be formed from any material which is selected from known materials generally used for the stent delivery system, as exemplified below: homopolymers of polytetramethyleneadipamide (nylon 46), polycaprolactam (nylon 6), polyhexamethyleneadipamide (nylon 66), polyhexamethylenesebacamide (nylon 610), polyhexamethylene dodecamide (nylon 612), polyundecanolactam (nylon 11), and polydodecanolactam (nylon 12); polyamide resins or copolymers, such as caprolactam/lauryllactam copolymer (nylon 6/12), caprolactam/aminoundecanoic acid copolymer (nylon 6/11), caprolactam/ω-aminonanoic acid copolymer (nylon 6/9), caprolactam/hexamethylenediammonium adipate copolymer (nylon 6/66), adipic acid-metaxylenediamine copolymer; and hexamethylenediamine-m-phthalic acid (or p-phthalic acid) copolymer, polyalkylene resins, such as polyethylene resin [including linear low-density polyethylene (LLDPE), low-density polyethylene (LDPE), and high-density polyethylene (HDPE)] and polypropylene resin; polyolefins, such as ethylene-propylene copolymer, ethylene-vinyl acetate copolymer, and their crosslinked products or partially crosslinked products (e.g., crosslinked ethylene-vinyl acetate copolymer); epoxy resin, urethane resin, diallyl phthalate resin (allyl resin), polycarbonate resin, fluororesin, amino resin (urea resin, melamine resin, benzoguanamine resin), polyester resin (e.g., polyethylene terephthalate), styrene resin, acrylic resin, polyacetal resin, vinyl acetate resin, phenolic resin, vinyl chloride resin, silicone resin, polyarylenesulfide (e.g., polyphenylenesulfide), silicone rubber, latex rubber, and nylon elastomer in the form of block copolymer composed of hard segments (which are nylon 6, nylon 66, nylon 11, or nylon 12) and soft segments (which are polyalkylene glycol, polyether, or aliphatic polyester). They may be used alone or in combination with one another. The above-mentioned polymeric materials may be commercial ones or purposely synthesized ones. The commercial products of the above-mentioned polyamide resins are exemplified by RILSAN (registered mark) AECNO TL nylon 12 (made by ARKEMA Co., Ltd.) and Grilamid L25 (made by EMS-CHEMIE Co., Ltd.). The commercial products of the above-mentioned nylon elastomer are exemplified by Grilflex ELG5660 and Grilflex ELG6260 (made by EMS-CHEMIE (Japan) Ltd.). Preferable among these materials are those which are capable of orientation. The balloon should preferably be one which is formed by biaxial orientation so that it has a sufficient strength to withstand relatively high internal pressure. That is, the balloon preferably exhibits relatively high tensile strength, as mentioned in detail below. The balloon may be formed by any known method, such as blow molding, extrusion molding, injection molding, rotational molding, transfer molding, press molding, and solution casting. Preferred among these methods are extrusion molding, blow molding, and injection molding, with blow molding being most desirable. Blow molding may be accomplished in various ways without being limited to the specific method mentioned below by way of example.

To be more specific, the balloon may be formed by biaxial blow molding as explained below. The first step in biaxial blow molding starts by drawing a tube (or a cylindrical body) made of the desired material to a prescribed length at an adequate temperature (say, 15° C. to 300° C.). This step draws the tube in its axial direction. In the second step, the drawn tube undergoes expansion in a mold, which has a cavity (for molding space) that approximately defines the shape which the balloon should have after expansion. Expansion of the tube in the mold is accomplished by introducing nitrogen gas under high pressure. Blowing in the second step expands the tube in the radial direction. As a result, the tube undergoes orientation in a direction different from the axial direction of orientation resulting from the first step. In this way, there is obtained the biaxially oriented balloon as desired. Orientation in the axial direction may be carried out after blowing or simultaneously with expansion of the tube in the mold, that is, with blowing in the mold. In this way, it is possible to readily produce balloons having relatively high dimensional accuracy with minimal variation in shape, membrane strength, and characteristic properties.

The hub unit 14 serves as an inlet port for injecting a fluid into the medical device 1. It is composed of a first hub 14a communicating with the first lumen 11a and a second hub 14b communicating with the second lumen 12a. The first hub 14a and the second hub 14b permit respective syringes to be connected to each of them for injection of fluid into the first lumen 11a and the second lumen 12a.

The first tubular body 11 is fluid-tightly connected to the far end of the main body of the hub unit 14. The main body of the hub unit 14 has a fluid passage formed therein which communicates with both the first lumen 11a and the first hub 14a. The second tubular body 12 penetrates through and fluid-tightly joins, or is fixed to, the near end of the main body of the hub unit 14 such that the free end (near end) of the second tubular body 12 projects toward the second hub 14b from the hub unit 14.

As mentioned above, the medical device 1 has two mutually independent fluid passages: one extending from the first hub 14a to the far end of the first tubular body 11 through the first lumen 11a; and one extending from the second hub 14b to the far end of the second tubular body 12 through the second lumen 12a. With this construction, there is no possibility that the fluid injected into one passage flows into the other passage.

The medical device 1 is not specifically restricted in dimensions. In the case of application to treatment of femoral fracture (to be mentioned later), the medical device is desirably dimensioned such that the first tubular body 11, with the expandable body 13 collapsed, is readily insertable into the hole formed by the K-wire. Such dimensions are usually 0.7 to 4.0 mm, preferably 1.0 to 2.0 mm. Moreover, the first tubular body 11 should preferably have a tapering shape such that its outside diameter gradually decreases from the near end to the far end. In this case, the first tubular body 11 should have a maximum outer diameter of 0.8 to 1.9 mm, preferably 0.7 to 1.6 mm (at the near end), and a minimum outer diameter of 0.4 to 1.4 mm, preferably 0.6 to 1.3 mm (at the far end). The first tubular body 11 of tapered shape is not specifically restricted in the ratio of the minimum outer diameter (at the far end) to the maximum outer diameter (at the near end). However, the ratio should correspond to the shape of the hole formed by the K wire. To be more specific, the ratio should be from 0.50 to 0.95, preferably from 0.60 to 0.90. The expandable body 13 in its expanded state should have an adequate outside diameter so that it permits the medical device 1 disclosed here to be firmly fixed to the inside wall of the hole formed by the K wire. The adequate outside diameter of the expandable body is substantially equal to or slightly larger than the diameter of the hole in which the medical device 1 is fixed. It is usually 2 to 5 mm, which is approximately equal to the outside diameter of the ordinary K wire. The first tubular body 11 should preferably have an overall length of 500 mm to 750 mm, which is substantially equal to or slightly larger than that of the ordinary K wire. Moreover, in the case of the medical device additionally having the second tubular body 12, the second tubular body 12 is not restricted in outer diameter so long as it relatively smoothly passes through the first lumen of the first tubular body 11. It should preferably have an outer diameter substantially equal to the outer diameter of the blood vessel in the hole formed by the K wire. The outer diameter of the second tubular body 12 is typically 0.2 to 3.0 mm, preferably 0.5 to 1.2 mm.

Figure 3:
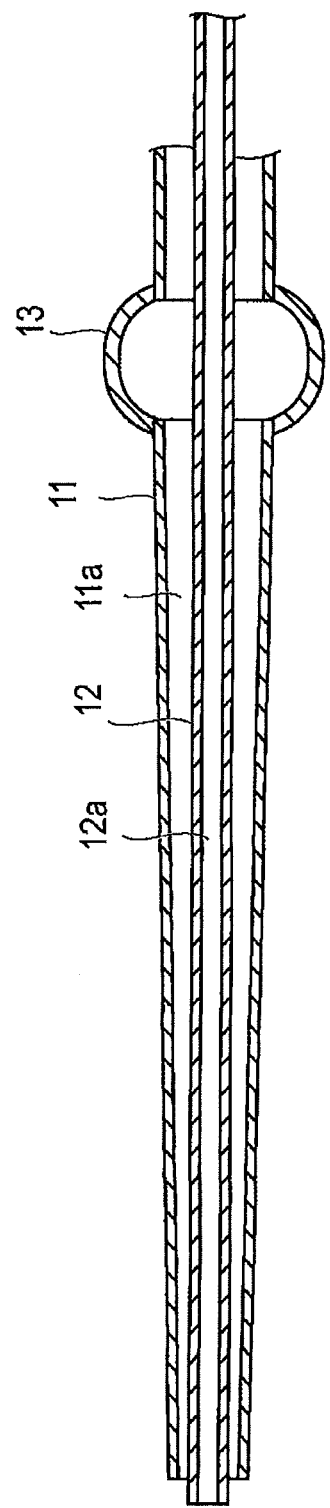
FIG. 3 is an enlarged view of a part of the medical device shown in FIG. 2.

FIG. 3 is an enlarged view of a part of the medical device shown in FIG. 2. It is noted that the first lumen 11a communicates with the space in the expandable body 13, so that the fluid injected into the first lumen 11a from the first hub 14a flows at least partly into the space in the expandable body 13. The fluid which has flowed into the space in the expandable body 13 exerts its pressure on the expandable body 13 to expand it radially outwardly in the direction perpendicular to the direction in which the medical device 1 extends (i.e., perpendicular to the direction of longitudinal extent of the medical device 1).

The second lumen 12a is uniform in outside diameter over its entire length; however, the first lumen 11a gradually decreases in outside diameter from its near end (right end) to its far end (left end). In other words, the first tubular body 11 gradually decreases in outside diameter (exhibits a tapered shape) from its near end (right end) to its far end (left end), assuming that it is uniform in wall thickness over its entire length.

The above-mentioned shape produces the result that the fluid injected into the first lumen 11a experiences resistance due to friction with the lumen wall such that the resistance increases toward the far end of the first lumen 11a and decreases to a minimum in the space in the expandable body 13. This causes a viscous fluid injected into the first lumen 11a to flow at least partly into the space in the expandable body 13. Thus, the expandable body 13 continues to expand until it takes on its prescribed shape.

In the example shown in FIG. 3, the first tubular body 11 includes two tubular bodies arranged so that the expandable body 13 is held or positioned between the two tubular bodies. In addition, the expandable body 13 has two openings, positioned at opposite axial ends of the expandable body 13, facing each other and joined in a liquid-tight manner to the two tubular bodies through the two openings as illustrated in FIG. 3. The example shown in FIG. 3 is not intended to restrict the method for joining together the first tubular body 11 (according to the embodiment) and the expandable body 13, but rather is just an example.

Figure 4:
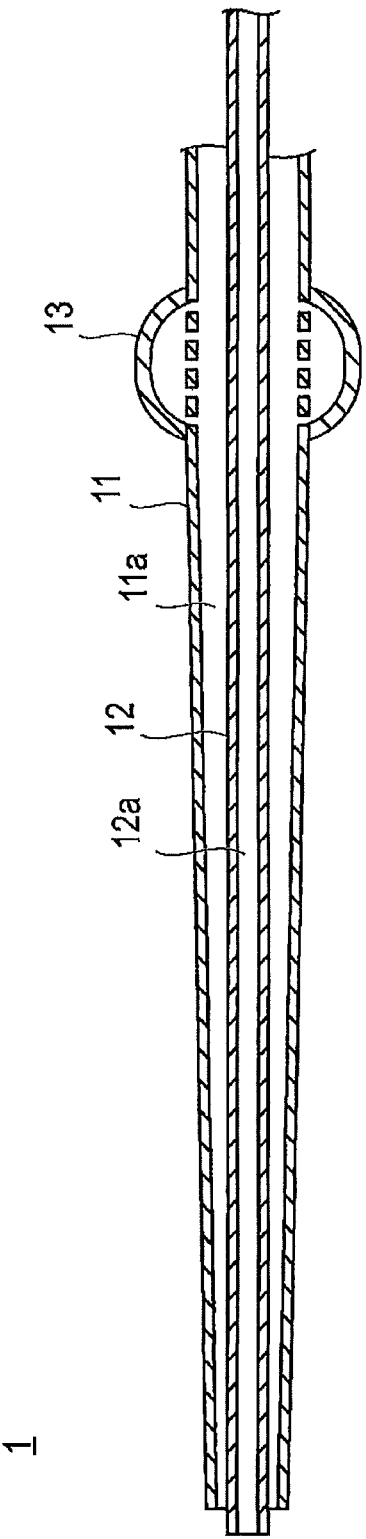
FIG. 4 is an enlarged view of a modified example of the medical device shown in FIG. 3.

FIG. 4 illustrates another example of a way of joining together or fixing together the first tubular body 11 and the expandable body 13. In the example shown in FIG. 4, the first tubular body 11 is a single tubular body that penetrates or passes through the expandable body 13, and part of the first tubular body 11 which is inside the expandable body 13 has a relatively large number of perforations that permit the space of the first lumen to communicate with the space of the expandable body 13. This structure helps prevent the first tubular body 11 from bending at the position where the expandable body 13 is arranged.

Figure 5:
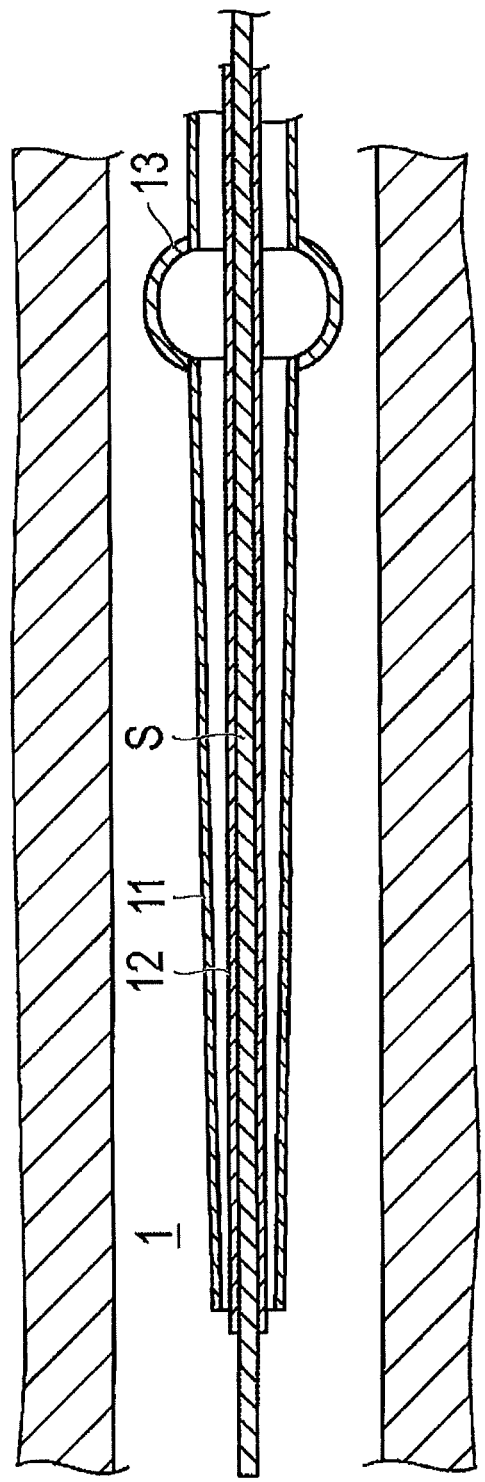
FIG. 5 is a longitudinal cross-sectional view of the medical device disclosed here showing one operational aspect during use.

Set forth next is a description of a method for using the medical device 1 according to the embodiment described above. The method is acceptable particularly in the case where the medical device 1 is used to inject two different kinds of gels into the hole of a living tissue. The procedure according to this method starts by arranging the medical device 1 horizontally in the hole as shown in FIG. 5 which is a cross-sectional view of a part of the medical device 1 inserted into or positioned in the hole. As shown in FIG. 5, the medical device 1 is arranged in the hole in such a way that at least the expandable body 13 is completely or fully located inside the hole. (The hatching in FIGS. 5 to 8 indicates living tissue surrounding the hole). It is desirable that the second lumen 12a hold the stylet S inserted therein which inhibits or prevents the second tubular body 12 from bending and also inhibits or prevents the gel from flowing from the far end of the second tubular body 12.

Subsequently, the first lumen 11a is supplied with the first gel injected from a syringe or the like connected to the first hub 14a. During injection, the first gel injected into the first lumen 11a flows at least partly into the space in the expandable body 13 until the expandable body 13 completely expands because the first lumen 11a exerts more resistance in going toward the far end. That is, the narrowing shape of the space between the outer surface of the second tubular body 12 and the inner surface of the first tubular body 11 resists or impedes the flow of the first gel and so the first gel more easily moves into and fills the expandable body 13. The first gel that has flowed into the expandable body 13 exerts an internal pressure on the expandable body to outwardly expand the expandable body 13 in the direction perpendicular to the axial direction.

Figure 6:
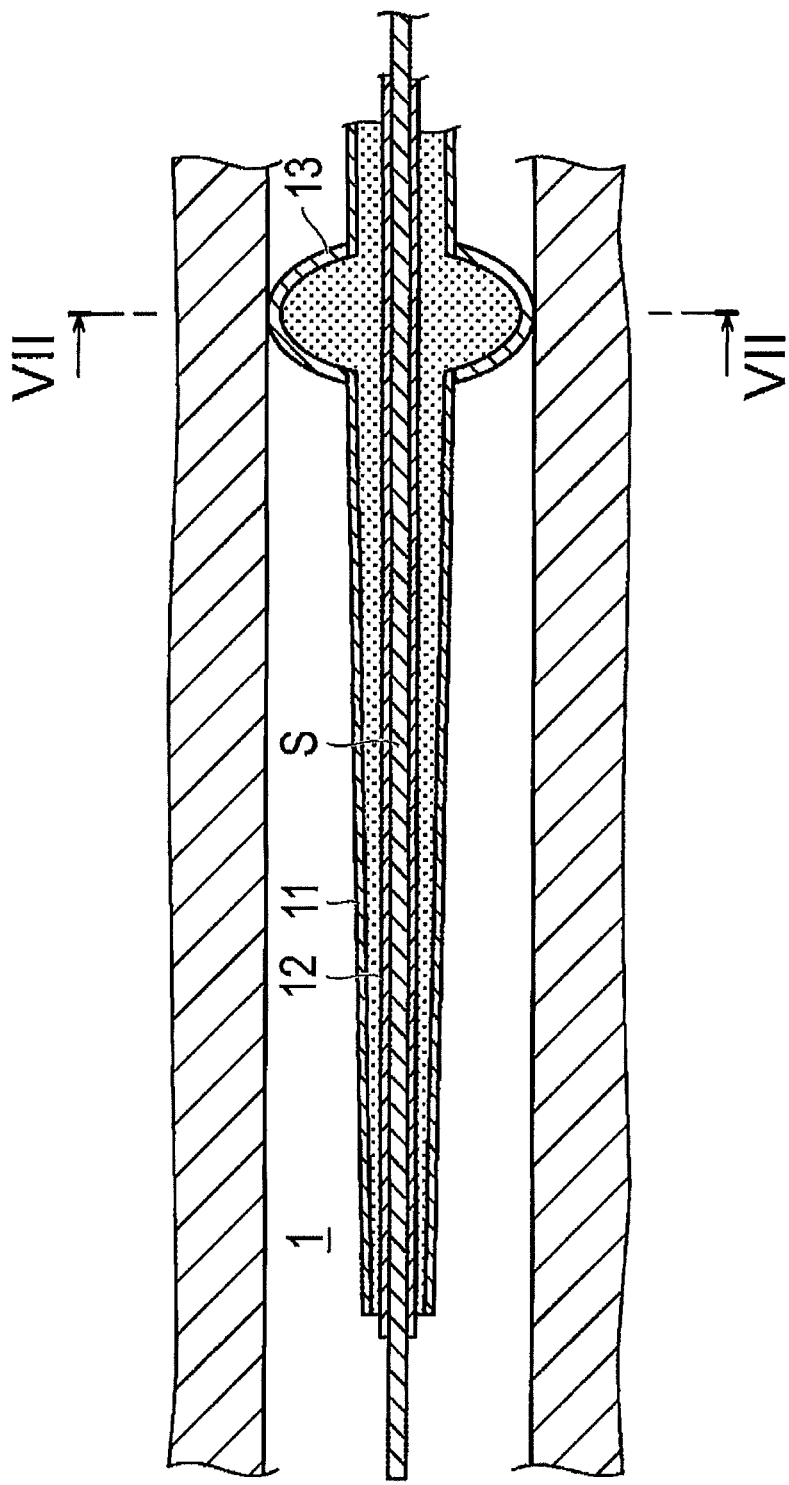
FIG. 6 is a longitudinal cross-sectional view of the medical device showing a different operational aspect during use.

As soon as the expandable body 13 expands to such an extent that its outside diameter equals the inside diameter of the hole, the medical device 1 is fixed in the hole. FIG. 6 shows the medical device fixed in the hole. The medical device 1 is securely fixed parallel to the hole because the outside wall or outer surface of the expandable body 13 pushes against the inside wall or inner surface of the hole.

Figure 7:
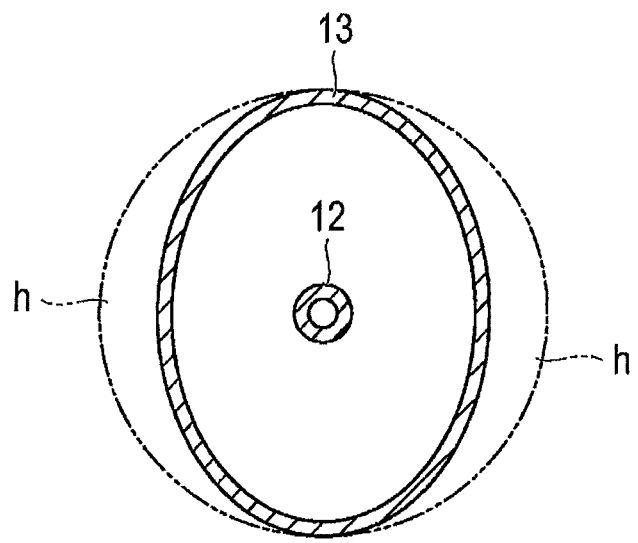
FIG. 7 is a cross-sectional view taken along the section line VII-VII in FIG. 6.
Figure 8:
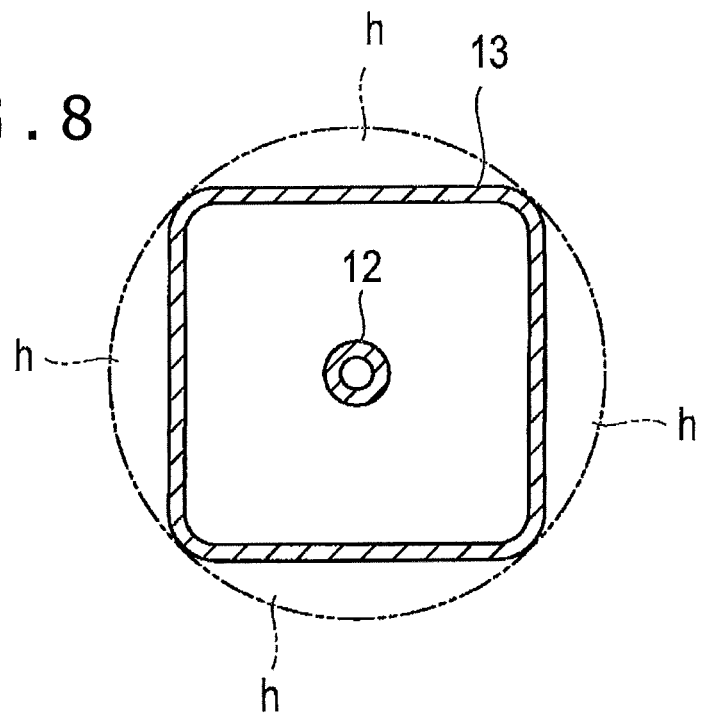
FIG. 8 is a cross-sectional view of a modified example of the expandable body of the medical device according to one embodiment disclosed here.

Referring to FIG. 7, the expandable body 13 should expand in such a way as to form exhaust passages (h) between the outer surface of the expandable body 13 and the inner surface of the hole (tissue surrounding the hole) so that gas escapes from the hole. The cross-sectional shape of the expandable body 13 is not limited to the ellipsoidal shape shown in FIG. 7 which is in contact with the inner surface of the hole (tissue surrounding the hole) as shown in FIG. 7. The expandable body 13 can be configured to take on any polygonal cross-sectional shape such as the one in contact with the inner surface of the hole (tissue surrounding the hole) as shown in FIG. 8.

Injection of the first gel into the first lumen 11a from the syringe is continued so that the first gel forms a tubular layer as the first layer in the hole. During this step, the exhaust passages (h) permit gas (air) to escape from the medical device 1 and the hole. After the first layer has formed, the stylet S is removed from the second lumen 12a.

Then, the second lumen 12a is filled with the second gel by injection from the syringe. At the same time, the medical device 1 is removed from the hole. In order to facilitate the removal of the medical device 1 from the hole filled with the first gel, it is desirable that the first tubular body should have surface treatment (treatment of the outer surface of the medical device 1) to prevent adhesion of the first gel. As a result of the foregoing procedure, there are formed in the hole the first layer (in tubular shape) of the first gel and the second layer (in rod-like shape) of the second gel arranged inside the first layer.

The medical device disclosed here has various uses in medicine as typically listed below.

(i) Prevention or remedy of ischemic disorder or congestion or alleviation of their symptoms, the ischemic disorder or congestion occurring in the region where the blood vessels in the bone are broken due to femoral fracture or any other fractures.

(ii) Remedy of ischemic disorder (or alleviation of its symptom) occurring in the lower limb.

(iii) Remedy of cirrhosis and hepatic infarct or alleviation of its symptom.

(iv) Remedy of bile duct cancer and alleviation of its symptom.

(v) Remedy of intracerebral bleeding and alleviation of its symptom.

In the case of remedying ischemic disorder (or alleviation of its symptom) occurring in the lower limb, the medical device disclosed here permits the first or second tubular body inserted in the direction of muscle extending from the knee to the heel to place the gel containing a drug to remedy ischemic disorder occurring in the lower limb.

In the case of remedying cirrhosis and hepatic infarct or alleviation of its symptom, the medical device allows placement or delivery of the gel containing a drug to remedy cirrhosis through the first or second tubular body when a wedge-shape focal lesion is found for its low absorption with abdominal CT scan. Cirrhosis (hepatic infarct) is focal necrosis of hepatocytes resulting from liver ischemic disorder no matter what its cause may be. One of the most common causes for cirrhosis is the occlusion of the hepatic artery. Most cases of cirrhosis are asymptomatic and left undiagnosed. So, some patients suffer from upper right bellyache, fervescence, nausea, and vomiting, and show the symptom of choloplania and a temporary rise in aminotransferase value. This has stimulated a strong demand for preventing and remedying cirrhosis and alleviating its symptom.

In the case of remedying bile duct cancer and alleviating its symptom, the medical device disclosed here allows placement of the gel containing a drug to remedy ischemic bile duct cancer through the first or second tubular body when ischemic disorder is found by liver function test or ultrasonography (mostly negative) or when ischemic bile duct cancer (which occurs after orthotopic liver transplantation) is found by cholangiography with MRI or endoscope. The ischemic bile duct cancer is a local ischemic disorder in the biliary system which results from any process that destroys the artery plexus around the bile duct. Common causes for the ischemic bile duct cancer include orthotopic liver transplantation (which is performed against thrombus in hepatic artery or damage due to rejection of transplantation to the plexus around the bile duct), chemical embolotherapy, radiotherapy, iatrogenic damage to hepatic artery, ligature for gallbladder resection with the help of a laparoscope, and thrombus due to hypercoagulability. Therefore, the ischemic bile duct cancer leads to cholestasis and sometimes accompanies bile duct necrosis, cholangitis, and biliary stenosis. This stimulated a strong demand for remedying and preventing ischemic bile duct cancer and alleviating the symptoms.

The medical device described above and illustrated in the drawing figures should preferably be applied to the cases (i) and (iii) above, most desirably to the case (i). Application to the case (i) will be described below in more detail.

A second embodiment disclosed here provides a method for vascularization in a bone hole which includes filling a hole formed in a bone with a first gel in such a way that the first gel forms a barrier on the inner surface of the bone hole, thereby forming a cavity in the axial direction of the hole, and filling the cavity with a second gel containing a vascularizing agent. A third embodiment involves a method for vascularization in a bone hole which includes inserting a rod containing a vascularizing agent into a bone hole and filling the space in the bone hole with a first gel that functions as a barrier.

Ischemic disorders resulting from femoral fracture pose a serious problem as mentioned above. To address this problem, a method is disclosed here for the treatment of ischemic disorders, particularly a method for treatment of ischemic disorders resulting from femoral fracture by vascularization in a hole in a spongy bone. It is assumed in the following description that the second and third embodiments mentioned above are applied to treatment of ischemic disorders resulting from femoral fracture by vascularization in a hole in a spongy bone. It is to be understood that the invention disclosed here is not limited to these applications but may be used for any other applications in the same way.

The second embodiment will be described with reference to the accompanying drawings. Although the following description is concerned with application to the osteosynthesis of the femur, the method explained below may be applied to uses other than treatment of ischemic disorders resulting from femoral fracture.

Figure 9A:
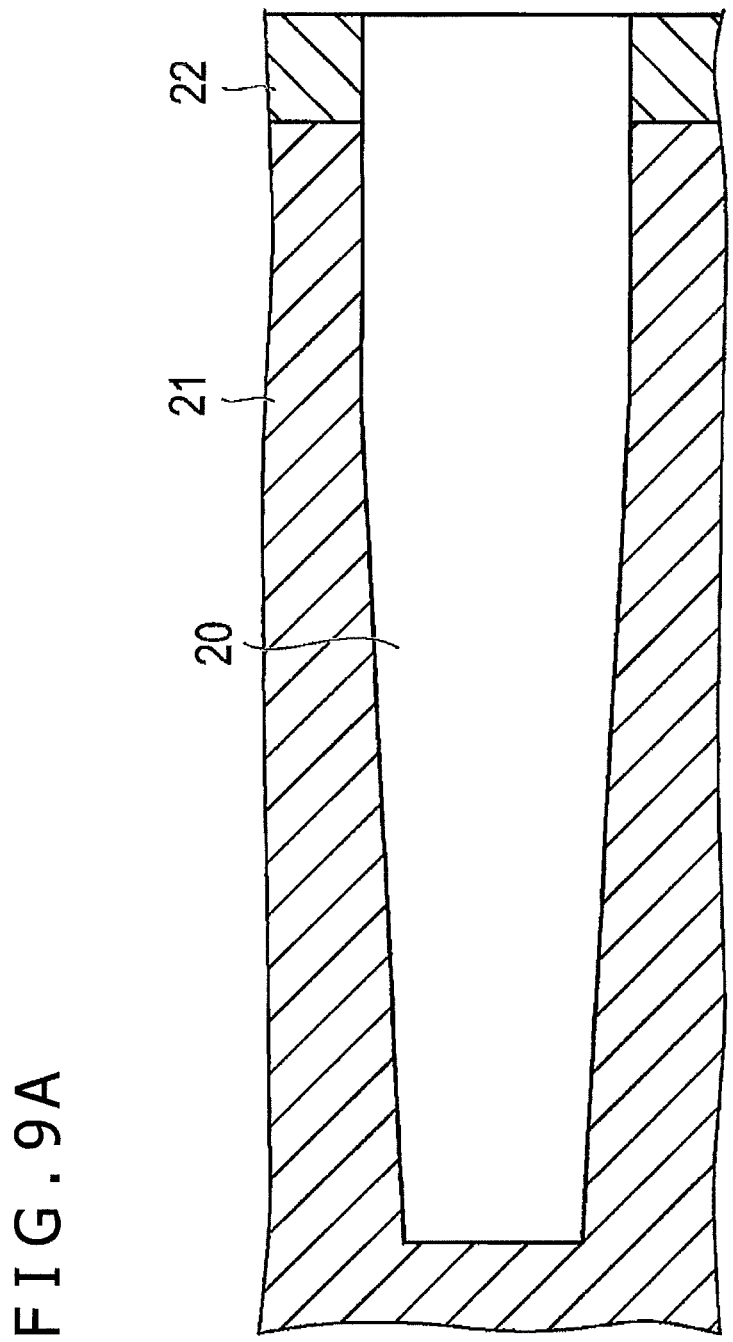
FIG. 9A is a cross-sectional view showing one operational aspect of a method for curing ischemic disorder associated with femoral fracture using the medical device disclosed here.

FIGS. 9A to 9H are cross-sectional views showing how to cure ischemic disorder due to femoral fracture by using the medical device disclosed here. The illustrated embodiment is intended to fix the fractured part with a screw type implant. The first step for this purpose starts with inserting a metal rod (like K wire) into the bone head from the side of the femur. In the next step, a screw type implant is advanced with the help of this K-wire, and the implant is screwed to the desired position. Finally, the K screw is removed. In this way there is formed the hole 20 in the bone by the K wire, extending from the cortical bone 22 to the spongy bone 21, as shown in FIG. 9A. In other words, the hole 20 is formed as the K wire is inserted into the bone head from the side of the femur.

Figure 9B:
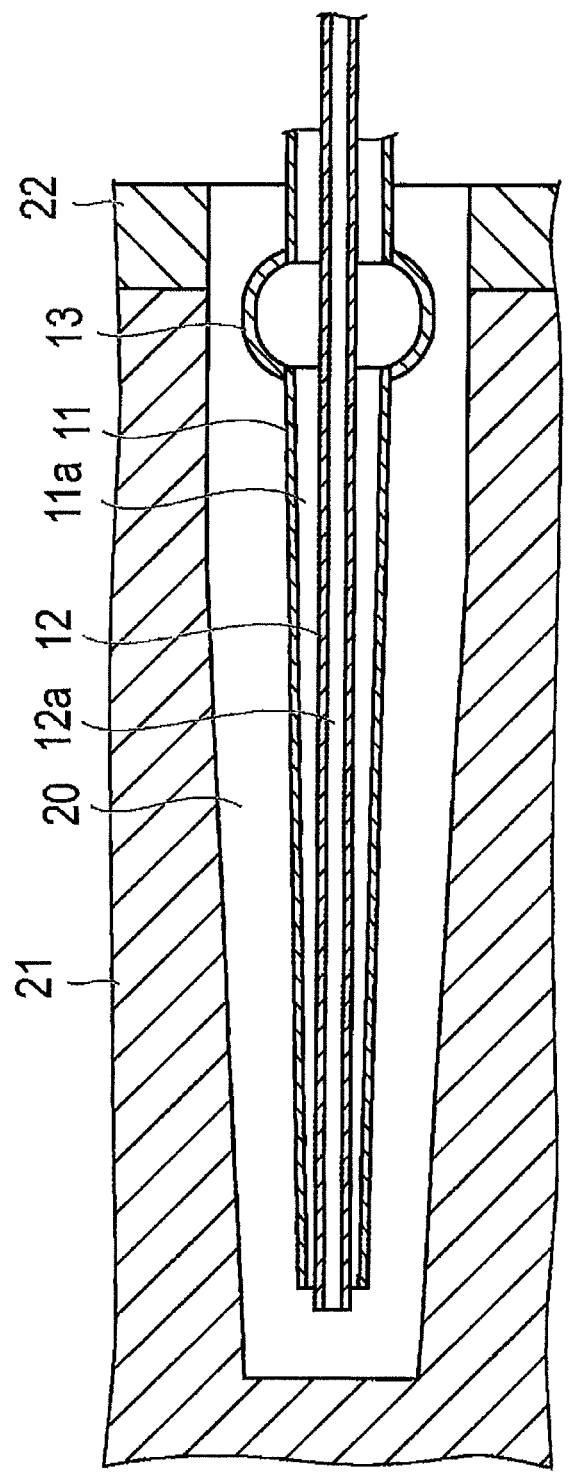
FIG. 9B is a cross-sectional view showing another operational aspect of a method for curing ischemic disorder associated with femoral fracture using the medical device disclosed here.

Subsequently, the medical device disclosed here is arranged in the hole 20 formed in the spongy bone 21, as shown in FIG. 9B. This step is called Step (a) for arrangement (arrangement step). In this step, the expandable body 13 remains unexpanded.

Figure 9C:
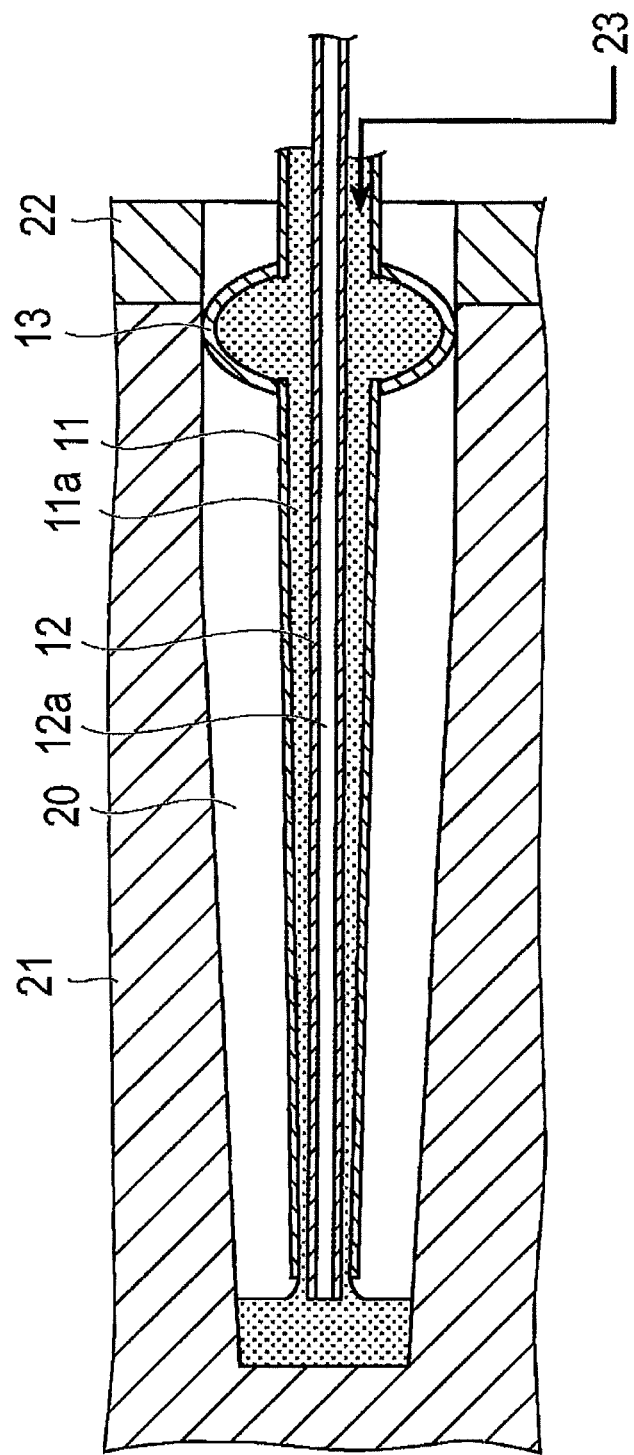
FIG. 9C is a cross-sectional view showing an additional operational aspect of a method for curing ischemic disorder associated with femoral fracture using the medical device disclosed here.

In the subsequent step shown in FIG. 9C, the hole formed in the spongy bone is filled with the first gel 23 in such a way that it forms a barrier on the inner wall of the spongy bone 21 and a cavity is formed in the axial direction of the hole. In other words, the hole 20 is filled with the first gel 23 through the first lumen 11a of the first tubular body 11 so that the first gel 23 forms a barrier on the inner wall of the spongy bone 21. This step is called Step (b) for filling the first gel (first gel filling step). The step for filling the first gel may be accomplished by any known method (using a syringe, for example), but it can be properly accomplished using the medical device disclosed here. That is, it is desirable to use the medical device 1 as shown in FIG. 9C. The first gel 23 is filled through the first lumen 11a of the first tubular body 11 in such a way that it forms a barrier between both of the spongy bone 21 and the cortical bone 22 and the second tubular body 12 (where vascularization will take place). Upon introduction of the first gel 23, the expandable body 13 expands in the direction perpendicular to the lengthwise direction due to the pressure of the first gel 23 introduced into the first lumen 11a, as shown in FIG. 9C. The expandable body 13 in its expanded state comes into close contact with the inner surface of the one surrounding the hole 20, thereby fixing the medical device in position relative to the hole. Since the expandable body 13 expands substantially symmetrically in the hole 20, the medical device is placed near the center of the hole 20. The thus positioned medical device permits the second gel containing a vascularizing agent to be delivered close to the center of the hole 20 when it is introduced into the second lumen 12a of the tubular body 12 in the subsequent Step (d). The result is that vascularization takes place near the center of the hole. FIG. 9C shows that the expandable body 13 comes into close contact with the inner wall or inner surface of the spongy bone 21 in the hole 20, thereby fixing the medical device to the hole, but there is another way of fixing the medical device to the hole by causing the expandable body to come into close contact with the inner wall or inner surface of the cortical bone 22 in the hole 20.

As mentioned above, it is desirable that the first tubular body 11 should have a tapered shape or gradually decreasing outside diameter (and inside diameter) so that the space between the inner surface of the first tubular body 11 and the outer surface of the second tubular body 12 gradually decreases in size from its near end to its far end. The tapered shape causes the first gel introduced into the first lumen 11a to experience more resistance due to friction with the inside wall of the tube as it advances to the far end of the first lumen 11a but to experience a minimum of resistance in the expandable body 13. The result is that the highly viscous fluid (first gel) introduced into the first lumen 11a flows at least partly into the expandable body 13, thereby expanding it until it comes into close contact with the inner wall of the hole. Owing to the tapered shape, the first tubular body 11 has a larger diameter at the near end, which facilitates introduction of the first gel, and the first tubular body 11 has a smaller diameter at the far end, which permits the second tubular body 12 to be placed (or vascularization to take place) near the center of the hole 20.

In Step (b) for filling the first gel, it is desirable to previously insert a core rod (stylet) (not shown) into the second lumen 12a of the second tubular body 12 before injecting the first gel 23 into the first lumen 11a of the tubular body 11. This prevents the first gel 23 from flowing backward into the second lumen 12a of the second tubular body 12.

The first gel 23 is not specifically restricted so long as it is capable of flowing into the first lumen 11a and expanding the expandable body 13 in the radially outward direction perpendicular to the lengthwise direction by the internal pressure of the first gel. The first gel 23 should preferably have the property that it is absorbed into the femur (the spongy bone 21 and the cortical bone 22) after vascularization by the second gel. For this reason, the first gel should preferably be formed from a biodegradable polymer, which is unrestrictedly selected from any known ones for medical use. Its typical examples are listed below: polyvinyl alcohol (PVA); cellulose derivatives, such as hydroxypropylmethylcellulose (HPMC), carboxymethylcellulose sodium (CMC-Na), and hydroxyethylcellulose (HEC); polysaccharides and derivatives thereof, such as chitin, thitosan, alginic acid, hyaluronic acid, agarose, starch, dextran, and pullulan, such polymers as carboxyvinyl polymer, polyethylene oxide, poly(meth)acrylamide, and poly(meth)acrylic acid, and their copolymer with polysaccharide; proteins and derivatives thereof, such as collagen and gelatin; glycosaminoglycan, such as heparin, chondroitin sulfate, dermatan sulfate, dextran sulfate, keratan sulfate, and heparin sulfate; and mucopolysaccharide. They may be used alone or in combination with one another.

In addition, the first gel 23 should preferably be compatible with the femur (the spongy bone 21 and the cortical bone 22) because it comes into direct contact with them. Consequently, it should preferably contain a bone-compatible substance, which may be selected from any of the known ones for medical use, such as calcium phosphate like hydroxyapatite. Such bone-compatible substances may be used alone or in combination with one another.

The first gel may be composed of biodegradable polymer and bone-compatible substance in any ratio so long as it is absorbed into the femur after vascularization by the second gel and it is compatible with the femur. The ratio of biodegradable polymer to bone-compatible substance should preferably be from 99:1 to 1:99, more preferably from 90:10 to 50:50 (by weight). The first gel specified above becomes integral with the femur because the bone-compatible substance contained in the barrier formed by the first gel is absorbed into the femur.

Figure 9D:
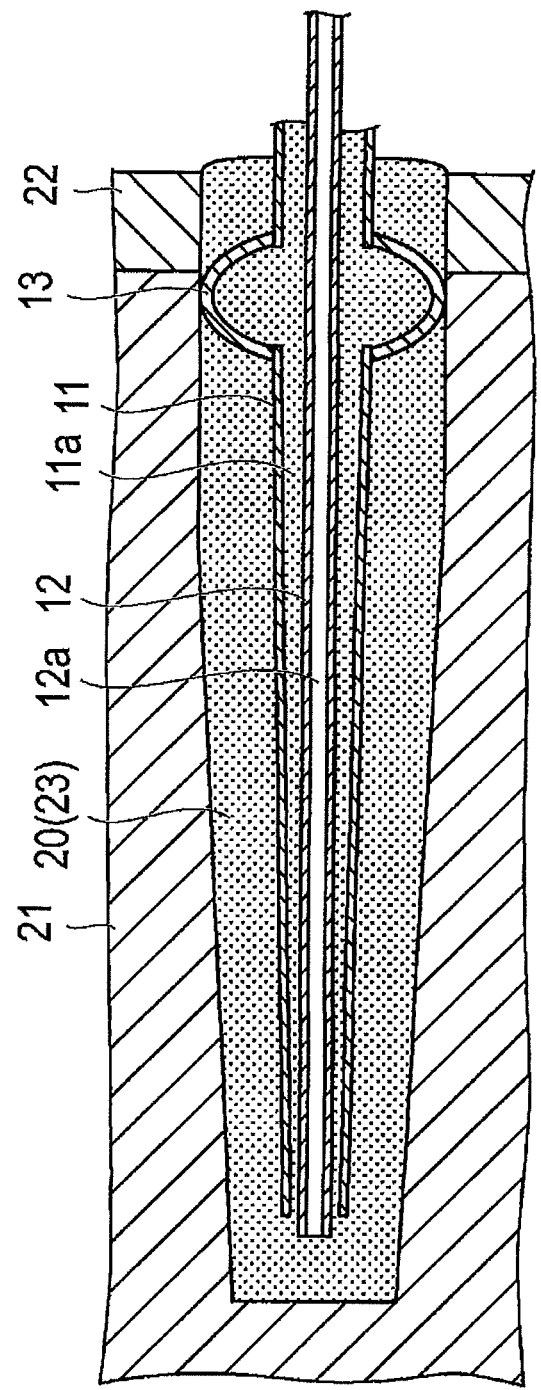
FIG. 9D is a cross-sectional view showing another operational aspect of a method for curing ischemic disorder associated with femoral fracture using the medical device disclosed here.

After the hole 20 has been completely filled with the first gel as shown in FIG. 9D, the first tubular body 11 is removed while the first gel is being injected. This step is called Step (c) for removing the first tubular body (removing step). Before the first tubular body 11 is removed, the expandable body 13 (in its expanded state as shown in FIG. 9D) should be collapsed. This facilitates removal of the first tubular body 11. With the first tubular body 11 removed, the hole 20, except for the space occupied by the second tubular body 12, is filled with the first gel 23 as shown in FIG. 9E. The first tubular body 11 may be removed in any other ways than mentioned above. For example, it is possible to remove the first tubular body 11 while holding the second tubular body 12 by hand or using a tool. It is also possible to remove the first tubular body 11 along an extending body attached to the base end of the second tubular body 12. In this case, the extending body should be more than twice as long as the first tubular body 11, so that the first tubular body 11 can be removed while the second tubular body 12 remains fixed.

Figure 9F:
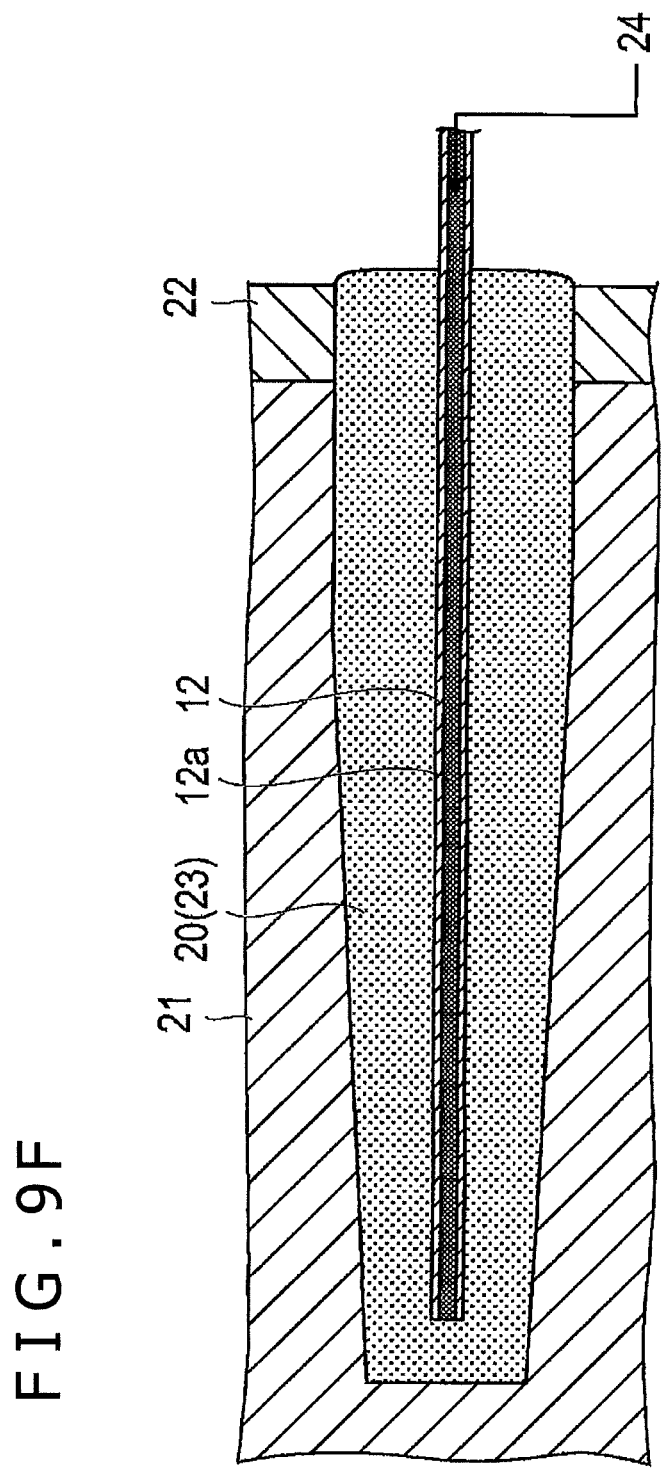
FIG. 9F is a cross-sectional view showing one operational aspect of a method for curing ischemic disorder associated with femoral fracture using the medical device disclosed here.
Figure 9G:
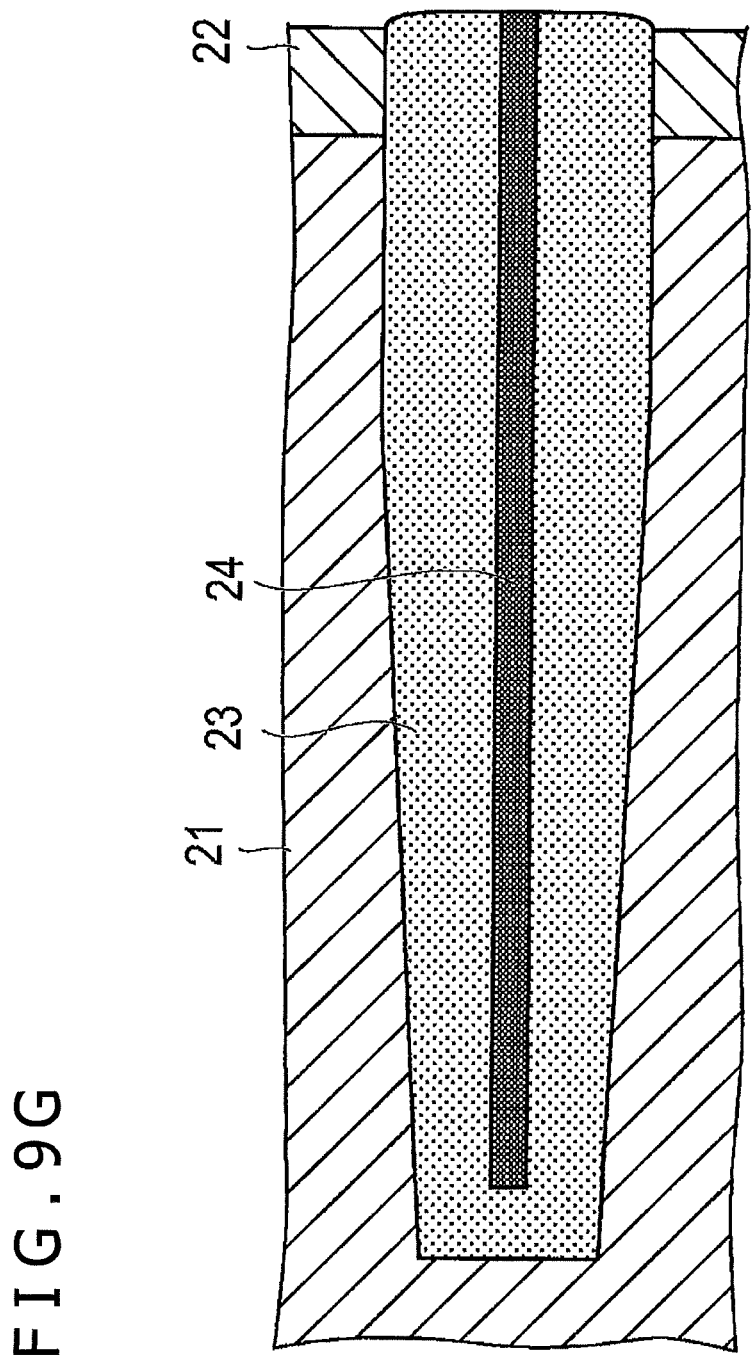
FIG. 9G is a cross-sectional view showing one operational aspect of a method for curing ischemic disorder associated with femoral fracture using the medical device disclosed here.

Subsequently, the hole which has been formed in Step (b) for filling the first gel is filled with the second gel containing a vascularizing agent. This step is accomplished by injecting the second gel 24 containing a vascularizing agent through the second lumen 12a of the second tubular body 12, as shown in FIG. 9F. This step is called Step (d) for filling the second gel (second gel filling step). It is desirable to inject the second gel while withdrawing the second tubular body, so that the hole is completely filled with the second gel as shown in FIG. 9G. The foregoing procedure may be replaced by one in which the second gel 24 containing a vascularizing agent is previously introduced into the second lumen 12a of the second tubular body 12 before the medical device is inserted into the hole 20. In this case, the core rod (stylet) is not necessary.

The second gel 24 for this step is not specifically restricted so long as it is capable of vascularization. It should preferably be one which is adsorbed into the femur (the spongy bone 21 and the cortical bone 22) after vascularization by the vascularizing agent. For this reason, the second gel should preferably contain a biodegradable polymer selected from any known ones for medical use as exemplified below: polysaccharides and derivatives thereof, such as chitin, thitosan, alginic acid, hyaluronic acid, agarose, starch, dextran, and pullulan, such polymers as carboxyvinyl polymer, polyethylene oxide, poly(meth)acrylamide, and poly(meth)acrylic acid, and their copolymer with polysaccharide; proteins and derivatives thereof, such as collagen and gelatin; glycosaminoglycan, such as heparin, chondroitin sulfate, dermatan sulfate, dextran sulfate, keratan sulfate, and heparin sulfate; and mucopolysaccharide. They may be used alone or in combination with one another.

It is desirable for the biodegradable polymer constituting the second gel to decompose faster than the one constituting the first gel, so that the former decomposes for absorption into the femur (the spongy bone 21 and the cortical bone 22) as vascularization by the vascularizing agent takes place in the hole formed by the second tubular body, and the latter decomposes more slowly for absorption into the femur (the spongy bone 21 and the cortical bone 22). Thus vascularization takes place nearly at the center of the hole 20. The biodegradable rate of the second gel to the first gel is not specifically restricted, but preferably from 0.99 to 0.01, more preferably from 0.33 to 0.66. Because of the different rate of decomposition, the first gel decomposes after vascularization, thereby allowing blood vessels to develop substantially at the center of the hole.

The second gel 24 contains a vascularizing agent, which is not specifically restricted but is selected from any known ones as exemplified below: vascular growth factor, such as VEGF121, VEGF165, and VEGF189; vascular endothelium growth factor (VEGF) family, (see J. Pathol. 1998; 184(1): 53-57.); fibroblast growth factor (FGF) family, (see Cell Biol. International 1995: 19(5): 431-444, and JACC 1993; 7: 2001-2006.); transforming growth factor (TGF)-$\alpha$ and $\beta$, (see Surg. Neurol. 1998; 49(2): 189-195.); platelet-derived growth factor (PDGF), (see Proc. Natl. Acad. Sci 1990; 87: 2628-2632, Annu. Rev. Cell Dev. Biol. 1995; 11:73-91, and Cancer Res. 1997; 57: 963-969.); and Ang 1 and Ang 2. They may be used alone or in combination with one another.

The second gel should contain the biodegradable polymer and the vascularizing agent in any ratio without specific restrictions so long as the former is absorbed into the femur as vascularization takes place. The vascularizing agent in the biodegradable polymer should account for 0.01 to 60 wt %, preferably 0.1 to 20 wt %, most desirably 0.2 to 10 wt %. This ratio is adequate for the biodegradable polymer to be absorbed into the femur as a result of vascularization. Moreover, this ratio is desirable for the vascularizing agent in the second gel to promote vascularization and for the biodegradable polymer in the second gel to be absorbed into the bone (living body) as vascularization proceeds.

The second lumen 12a is not specifically restricted in shape; however, a rod-shaped (cylindrical) configuration is preferable in consideration of the fact that vascularization takes place in it. In addition, the second lumen 12a is not specifically restricted in diameter; however, it should preferably have substantially the same diameter of as the blood vessel for vascularization. Its adequate diameter is 0.2 to 3.0 mm, preferably 0.5 to 1.2 mm. The second lumen 12a is not specifically restricted in length so long as it is long enough for vascularization to take place in the hole. It should be substantially equal to or slightly longer than the length of the hole 20 in its axial direction.

Figure 9H:
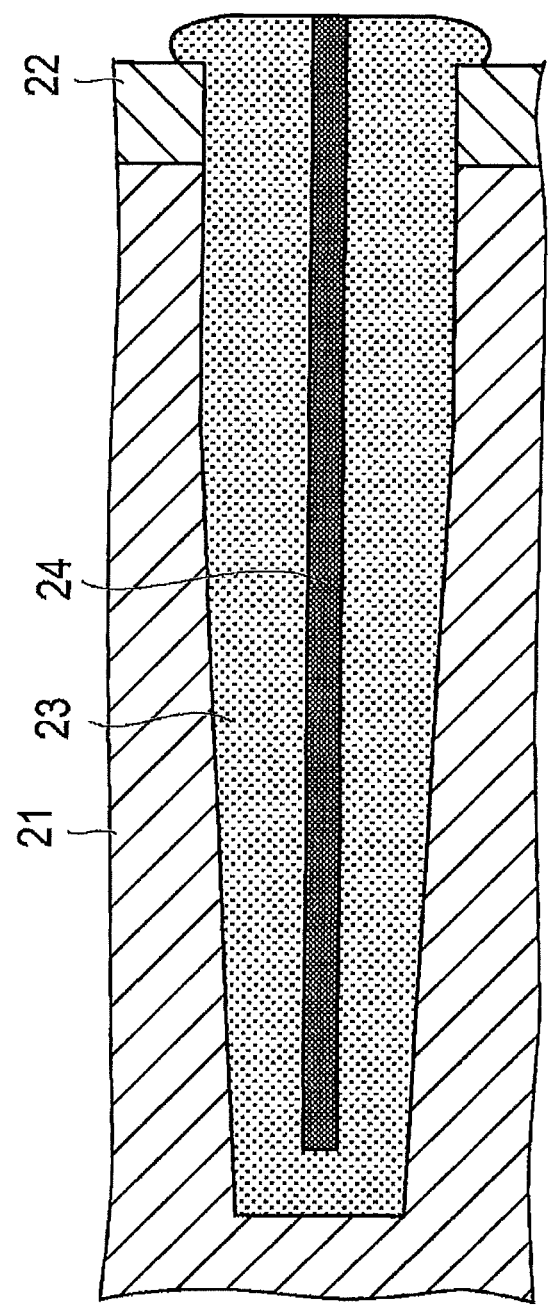
FIG. 9H is a cross-sectional view showing one operational aspect of a method for curing ischemic disorder associated with femoral fracture using the medical device disclosed here.

It is desirable that the first gel should cover the surface of the cortical bone 22 as shown in FIG. 9H. Vascularization is promoted by broadly covering the surface of the cortical bone 22 with the first gel compatible with the femur (the spongy bone 21 and the cortical bone 22). After the medical device of the present invention has been withdrawn, the wound is closed in the same way as employed in ordinary surgery.

The above-mentioned method permits the barrier to be formed from the first gel (containing a substance highly compatible with the spongy bone and the cortical bone) in the hole drilled in the spongy bone by the K wire and also permits the cylindrical (rod-shaped) object to be formed from the second gel (containing a vascularizing agent) in the cavity formed at the center of the barrier. In other words, the hole drilled in the spongy bone (or the hole remaining in the fractured part after removal of the K wire) is filled with a double-layered object composed of an outer layer of the first gel highly compatible with the spongy bone and an inner layer of the second gel containing a vascularizing agent. Thus the above-mentioned method permits vascularization to take place with the help of the second gel, thereby renewing the blood vessel. Therefore, the method according to the present invention is expected to restore the blood flow into the bone head, thereby effectively curing ischemic disorders.

According to the third embodiment, a method for vascularization in a bone hole includes the steps of inserting a rod containing a vascularizing agent into a hole in a bone and filling the void in the hole with a first gel which functions as a barrier. This third embodiment will be described with reference to FIGS. 10A-10F. Set forth below is a description of a method applied to osteosynthesis of the femur, but the method disclosed here is not limited in this regard and may be applied to uses other than treatment of ischemic disorders resulting from femoral fracture.

Figure 10A:
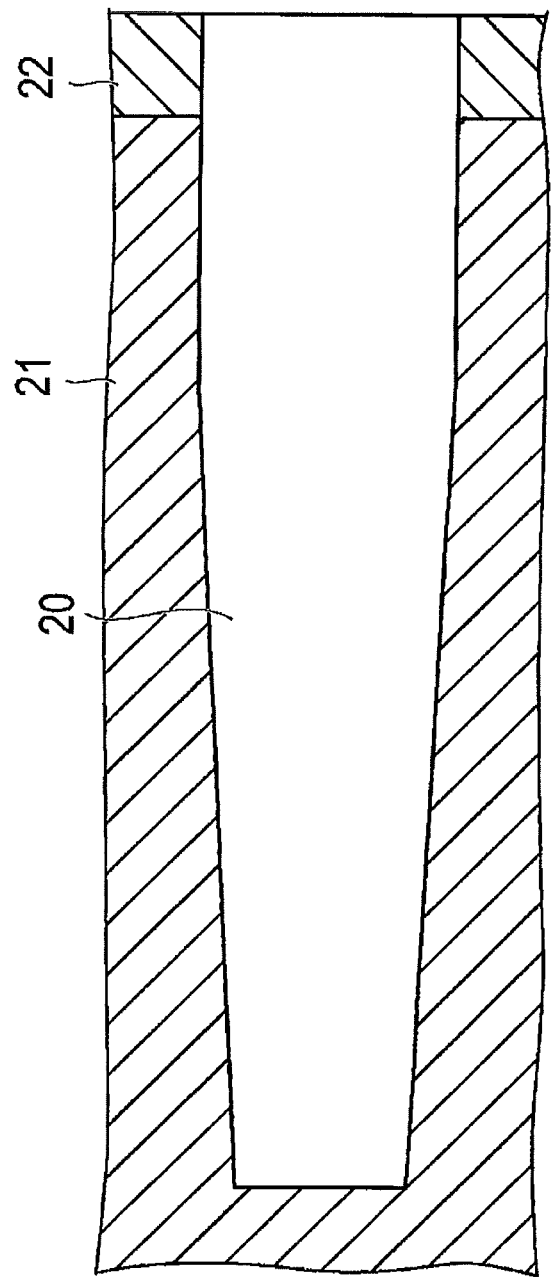
FIG. 10A is a cross-sectional view showing an operational aspect of another method of using the medical device disclosed here for curing ischemic disorder associated with femoral fracture.

FIGS. 10A to 10F illustrate another way of using the medical device disclosed here to cure ischemic disorders due to femoral fracture. The illustrated embodiment is intended to fix the fractured part with a screw type implant. The first step involves inserting a metal rod (like K wire) into the bone head from the side of the femur. In the next step, a screw type implant is advanced with the help of this K-wire, and the implant is screwed to the desired position. Finally, the K screw is removed. In this way there is formed the hole 20 in the bone by the K wire, the hole extending from the cortical bone 22 to the spongy bone 21, as shown in FIG. 10A. In other words, the hole 20 is formed as the K wire is inserted into the bone head from the femur side.

Figure 10B:
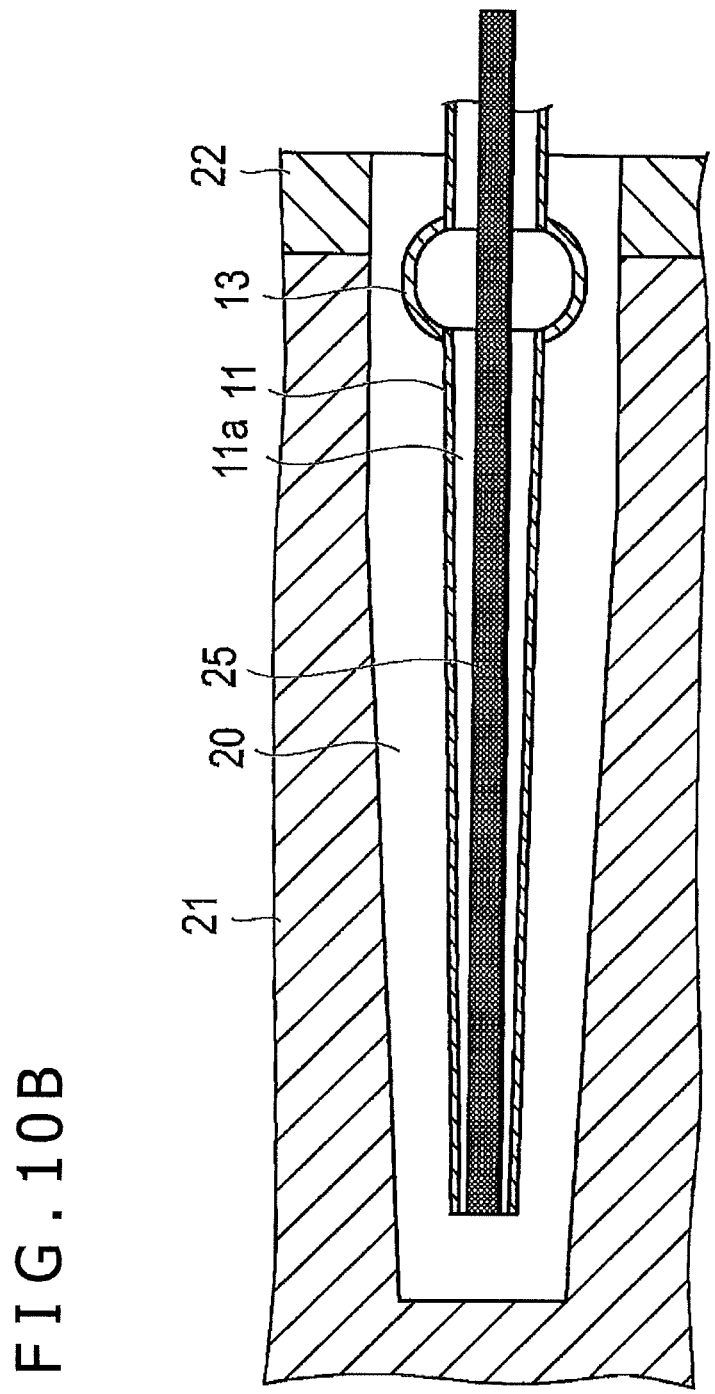
FIG. 10B is a cross-sectional view showing an operational aspect of another method of using the medical device disclosed here for curing ischemic disorder associated with femoral fracture.

Subsequently, the rod 25 containing a vascularizing agent is arranged in the hole (20) formed in the spongy bone 21, as shown in FIG. 10B. This step is called Step (i) for arrangement (arrangement step). According to this embodiment, this step is facilitated by using the medical device composed only of the first tubular body 11 (which has the first lumen 11a for a fluid to be injected from the opening at one end of the first tubular body 11 and to be discharged from the opening at the other end of the first tubular body 11) and the expandable body 13 formed on the first tubular body 11. The medical device is used in such a way that the first tubular body 11 is arranged in the hole 20, with the rod 25 inserted in the first lumen 11a of the first tubular body 11, as shown in FIG. 10B. In this step, the expandable body 13 remains unexpanded.

Subsequently, as mentioned below in more detail, the first gel 23 is injected into the first lumen 11a to apply an internal pressure to the expandable body 13 for its radially outward expansion in the direction perpendicular to the lengthwise direction. The thus expanded expandable body 13 comes into close contact with the inner wall or inner surface surrounding the hole 20, thereby fixing the medical device in the hole. At this time, the expandable body 13 expands substantially symmetrically in the hole 20, thereby allowing the rod 25 to be arranged nearly at the center of the hole 20. This embodiment can also be executed by arranging the rod 25 in the hole 20 (preferably close to the center of the hole 20) without using the medical device.

The rod 25 for this step is not specifically restricted so long as it is capable of vascularization. It should preferably be one which is adsorbed into the femur (the spongy bone 21 and the cortical bone 22) after vascularization by the vascularizing agent. For this reason, the rod 25 should preferably contain a biodegradable polymer and a vascularizing agent. The biodegradable polymer may be selected from any known materials for medical use, such as those listed in the description of Step (d) for filling the second gel (the second gel filling step). They may be used alone or in combination with one another.

The rod 25 contains a vascularizing agent, which is not limited to a specific material, but is selected from any known materials such as those mentioned above in the description of Step (d) for filling the second gel (the second gel filling step). The materials may be used alone or in combination with one another. The vascularizing agent in the biodegradable polymer should account for 0.01 to 40 wt %, preferably 0.1 to 10 wt %, most desirably 0.2 to 7 wt %. This ratio is not particularly restricted as long as the biodegradable polymer is adsorbed into the femur as a result of vascularization.

The rod 25 may be prepared in any known method as such or with modifications. For example, one method includes mixing together a biodegradable polymer and a vascularizing agent, forming the resultant mixture into a prescribed shape, and solidifying the formed product by dehydration. Another method includes filling a biodegradable polymer into a tube of proper size, solidifying it in the tube, removing the solidified product from the tube, and dipping it in a solution containing a vascularizing agent for adsorption, followed by drying.

The rod 25 is not limited to a particular shape, though an elongated shape or rod-shape (cylindrical shape) is preferable in consideration of the fact that vascularization takes place in it. In addition, the rod 25 is not specifically restricted in outer diameter, though it should preferably have substantially the same diameter of as the blood vessel to be vascularized. An adequate diameter is 0.2 to 3.0 mm, preferably 0.5 to 1.2 mm. The rod 25 is also not limited to a specific length so long as it is long enough for vascularization to take place in the hole. It should be substantially equal to or slightly longer than the length of the hole 20 in its axial direction.

Figure 10C:
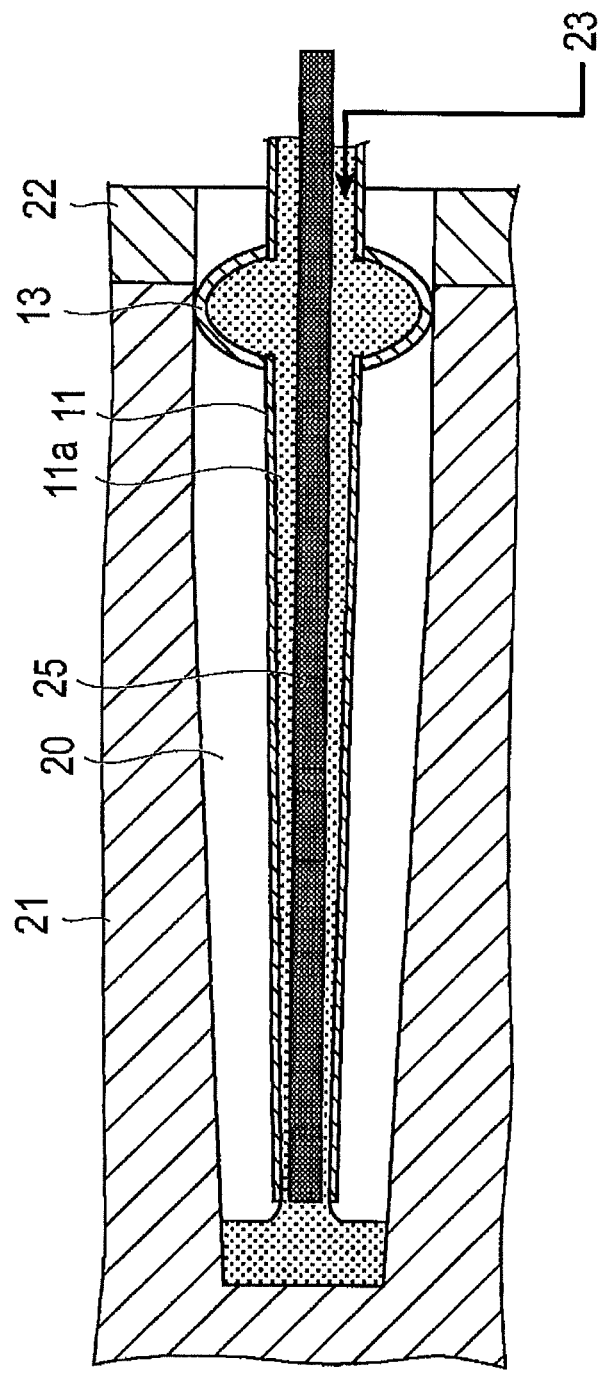
FIG. 10C is a cross-sectional view showing an operational aspect of another method of using the medical device disclosed here for curing ischemic disorder associated with femoral fracture.

In the subsequent step shown in FIG. 10C, the hole 20 formed in the spongy bone (the space excluding the rod 25) is filled with the first gel 23 in such a way that it forms a barrier between the rod 25 and the inner wall of the spongy bone 21. This is called Step (ii) for filling the first gel (first gel filling step). The filling with the first gel may be accomplished by any known method using a syringe but it is desirable to use the medical device described above. In other words, the filling with the first gel 23 should preferably be accomplished through the first lumen 11a of the first tubular body 11 of the medical device as shown in FIG. 10C. Upon introduction of the first gel 23, the expandable body 13 expands in the radially outward direction perpendicular to the lengthwise direction due to the pressure of the first gel 23 introduced into the first lumen 11a, as shown in FIG. 10C. The expandable body 13 in its expanded state comes into close contact with the inner wall of the hole 20, thereby fixing the medical device to the hole. Since the expandable body 13 expands substantially symmetrically in the hole 20, the medical device is placed near the center of the hole 20. The thus positioned medical device permits vascularization to take place close to the center of the hole. FIG. 10C shows that the expandable body 13 comes into close contact with the inner wall or inner surface of the spongy bone 21 in the hole 20, thereby fixing the medical device to the hole. But there is another way of fixing the medical device to the hole by causing the expandable body to come into close contact with the inner wall or inner surface of the cortical bone 22 in the hole 20.

As mentioned above, it is desirable that the first tubular body 11 should have a tapered shape or gradually decreases in outside diameter from its near end to its far end so that the space filled by the first gel gradually narrows from the near end to the far end. The tapered shape causes the first gel introduced into the first lumen 11a to experience more resistance due to friction with the inside wall of the tube as it advances to the far end of the first lumen 11a but to experience a minimum of resistance in the expandable body 13. The result is that the highly viscous fluid introduced into the first lumen 11a flows at least partly into the expandable body 13, so that the expandable body 13 radially outwardly expands until it comes into close contact with the inner wall of the hole. Owing to the tapered shape, the first tubular body 11 has a larger diameter at the near end, which facilitates introduction of the first gel, and the first tubular body 11 has a smaller diameter at the far end, which permits the rod 25 to be placed (or vascularization to take place) near the center of the hole 20. Therefore, the first tubular body 11 should preferably have a diameter at its far end which is substantially equal to or slightly larger than the diameter of the rod 25. This permits the rod 25 to be securely fixed by the first tubular body.

The first gel 23 is not specifically restricted so long as it is capable of flowing into the first lumen 11a and radially outwardly expanding the expandable body 13 in the direction perpendicular to the lengthwise direction. The first gel 23 should preferably have the property that it is absorbed into the femur (the spongy bone 21 and the cortical bone 22) after vascularization by the rod 25. For this reason, the first gel should preferably contain a biodegradable polymer, which is selected from any known materials for medical use, such as those listed in the above description of Step (b) for filling the first gel (first gel filling step). The materials may be used alone or in combination with one another.

In addition, the first gel 23 should preferably be compatible with the femur (the spongy bone 21 and the cortical bone 22) because it comes into direct contact with the femur. Consequently, it should preferably contain a bone-compatible substance, which may be selected from any known ones for medical use, such as those listed in the above description of Step (b) for filling the first gel (first gel filling step). Such bone-compatible substances may be used alone or in combination with one another.

The first gel may be composed of biodegradable polymer and bone-compatible substance in any ratio so long as it is absorbed into the femur after vascularization by the second gel and it is compatible with the femur. The ratio of biodegradable polymer to bone-compatible substance should preferably be from 99:1 to 1:99, more preferably from 90:10 to 50:50 (by weight). Such mixing ratios are desirable because the barrier formed from the first gel is absorbed into the femur as the second gel brings about vascularization. In addition, the barrier formed from the first gel exhibits an adequate degree of compatibility with the femur.

In the case where the rod 25 contains a biodegradable polymer and a vascularizing agent, it is desirable for the biodegradable polymer in the rod 25 to decompose faster than the biodegradable polymer constituting the first gel, so that biodegradable polymer in the rod 25 decomposes for absorption into the femur (the spongy bone 21 and the cortical bone 22) as the vascularizing agent brings about vascularization. The biodegradable polymer in the first gel decomposes at a slower rate for absorption into the femur (the spongy bone 21 and the cortical bone 22). Thus vascularization takes place nearly at the center of the hole 20. The biodegradable rate of the second gel to the first gel is not specifically limited, but is preferably from 0.01 to 0.99, more preferably from 0.33 to 0.66. Because of the different rate of decomposition, the first gel decomposes after vascularization, thereby allowing blood vessels to develop substantially at the center of the hole.

Figure 10D:
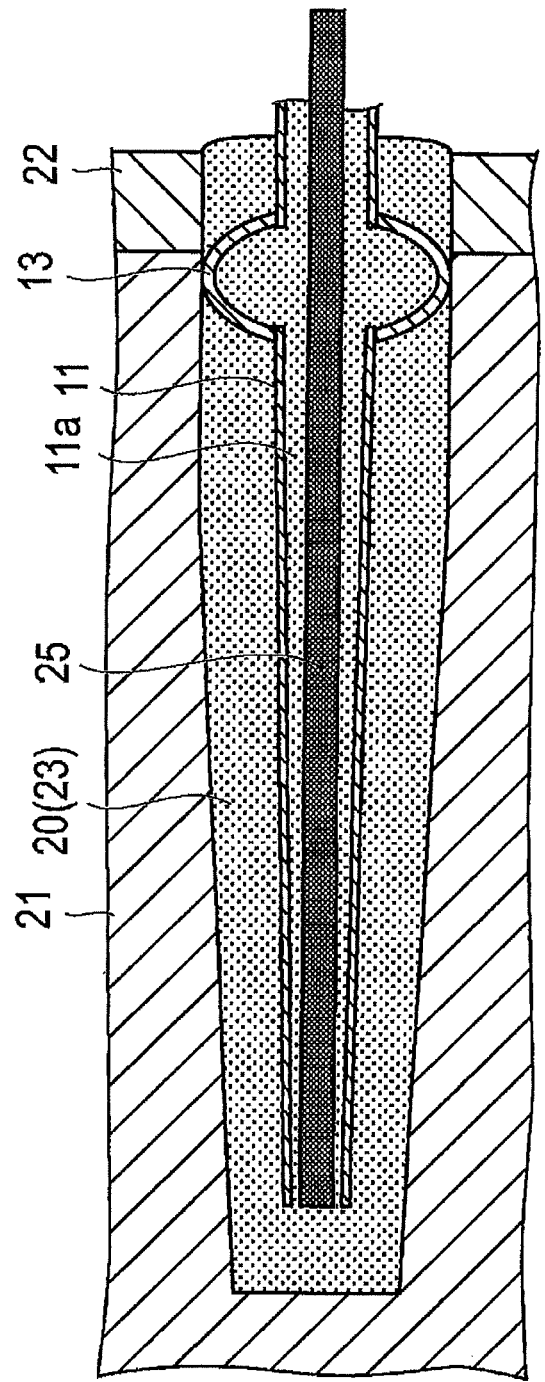
FIG. 10D is a cross-sectional view showing an operational aspect of another method of using the medical device disclosed here for curing ischemic disorder associated with femoral fracture.

After the hole 20 has been completely filled with the first gel as shown in FIG. 10D, the first tubular body 11 is removed while the first gel is being injected. This step is called Step (iii) for removing the first tubular body. With the first tubular body 11 removed, the hole 20, except for the space occupied by the rod 25, is filled with the first gel 23 as shown in FIG. 10E.

Figure 10F:
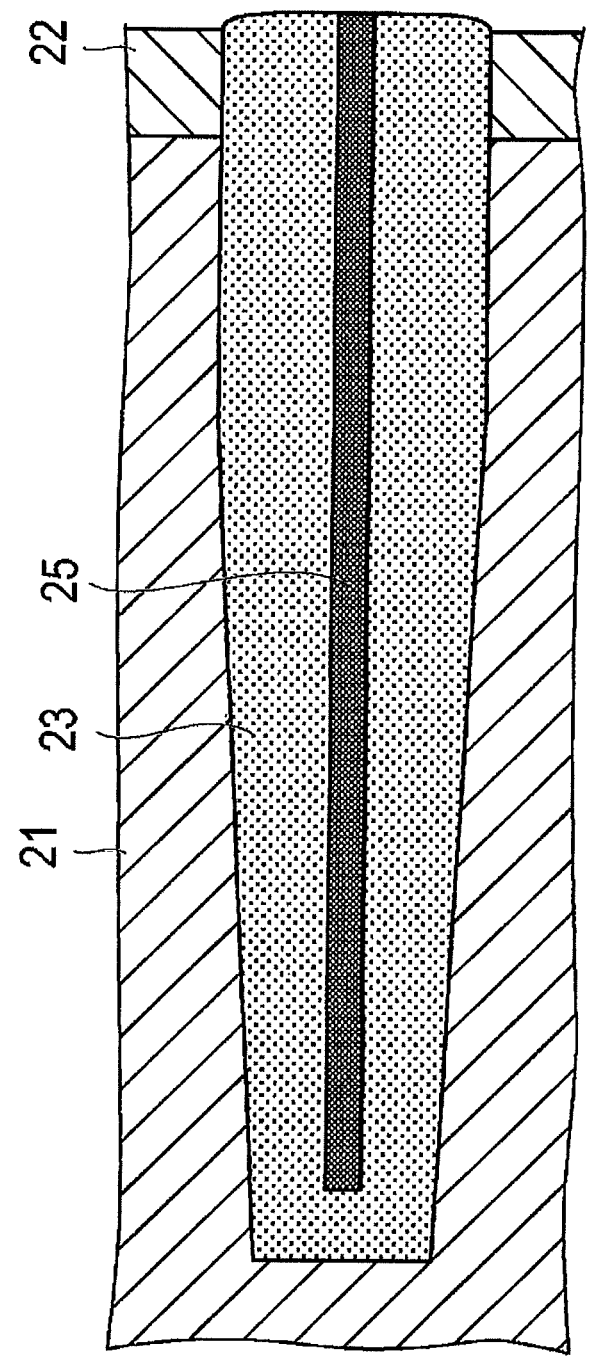
FIG. 10F is a cross-sectional view showing an operational aspect of another method of using the medical device disclosed here for curing ischemic disorder associated with femoral fracture.

It is desirable that the first gel should cover the inner surface of the cortical bone 22 as shown in FIG. 10E. Vascularization is promoted by broadly covering the surface of the cortical bone 22 with the first gel compatible with the femur (the spongy bone 21 and the cortical bone 22). In the case where the rod 25 projects from the part which is filled with the first gel as shown in FIG. 10D, the projecting part shown in FIG. 10E may be cut off as shown in FIG. 10F.

After the medical device has been withdrawn, the wound is closed in the same way as employed in ordinary surgery.

The above-mentioned method permits the barrier to be formed from the first gel (containing a substance highly compatible with the spongy bone and the cortical bone) in the hole drilled in the spongy bone by the K wire and also permits the cylindrical (rod-shaped) object to be formed from the second gel (containing a vascularizing agent) in the cavity formed at the center of the barrier. In other words, the hole drilled in the spongy bone (or the hole remaining in the fractured part after removal of the K wire) is filled with a double-layered object composed of an outer layer of the first gel highly compatible with the spongy bone and an inner layer of the second gel containing a vascularizing agent. Thus the above-mentioned method permits vascularization to take place with the help of the second gel, thereby renewing the blood vessel. The method disclosed here is expected to restore the blood flow into the bone head, thereby effectively curing ischemic disorders.

The detailed description above describes features, aspects and characteristics of a medical and vascularization method. The invention is not limited, however, to the precise embodiments and variations described above and illustrated in the drawing figures. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A medical device positionable in a hole in a bone of a human body, the medical device comprising:

a first tubular body possessing a size and configuration permitting the first tubular body to be positioned in the hole in the bone of the human body;

a lumen extending through the first tubular body, the lumen possessing a first opening at one end of the lumen permitting a liquid to be introduced into the lumen and also possessing a second opening at an opposite end of the lumen permitting the liquid in the lumen to be discharged from the lumen and into the hole in the bone, the lumen possessing an inner circumference at the second opening;

an expandable body fixed to the first tubular body and surrounding an interior space in fluid communication with the lumen in the first tubular body so that the liquid in the lumen of the first tubular body flows into the interior space of the expandable body and outwardly expands the expandable body to cause the expandable body to contact an inner surface of the bone surrounding the hole to fix the medical device in position in the hole in the bone;

an inner diameter of the lumen possessing a size which gradually decreases from the expandable body toward the second opening at the opposite end of the lumen so that the liquid introduced into the lumen by way of the first opening at the one end of the lumen and flowing toward the second opening at the opposite end of the lumen enters the interior space of the expandable body and outwardly expands the expandable body into contact with the inner surface of the bone surrounding the hole;

a second tubular body positioned in the lumen and possessing an outer circumference at a distal-most end of the second tubular body; and wherein the outer circumference of the second tubular body at the distal-most end of the second tubular body is smaller than the inner circumference of the lumen at the second opening so that the liquid in the lumen is dischargeable from the second opening and into the hole in the bone when the second tubular body is positioned at the second opening.

2. The medical device according to claim 1, wherein the lumen is a first lumen, and further comprising a second lumen extending through the second tubular body, the second lumen possessing a third opening at one end of the second lumen permitting a vascularizing agent to be introduced into the second lumen and also possessing a fourth opening at an opposite end of the second lumen, the second tubular body having an outer dimension smaller in size than the size of the first lumen so that a space exists between an outer surface of the second tubular body and an inner surface of the first tubular body, the space possessing a size which gradually decreases from the expandable body toward the second opening at the opposite end of the first lumen.

3. The medical device as defined in claim 1, wherein the expandable body is configured so that when the expandable body expands to an expanded configuration by the fluid introduced into the interior space, the expanded configuration is non-spherical so that a channel for discharge of gas exists between an inner wall of the hole and an outer surface of the expandable body.

4. The medical device as defined in claim 1, wherein the tubular body has surface treatment on its outer surface to prevent adhesion of the fluid to the tubular body.

5. A medical device positionable in a hole in a bone of a human body, the medical device comprising:
- a first tubular body possessing a size and configuration permitting the first tubular body to be positioned in the hole in the bone of the human body;
- a first lumen extending through the first tubular body, the first lumen possessing a proximal opening at proximal end of the first lumen permitting a liquid to be introduced into the first lumen and possessing a distal opening at a distal end of the first lumen permitting the liquid in the first lumen to be discharged from the lumen and into the hole in the bone, the first lumen possessing an inner circumference at the distal end of the first lumen;
- a second tubular body positioned in the first lumen, and a second lumen extending through the second tubular body, the second lumen possessing a proximal opening at proximal end of the second lumen and possessing a distal opening at a distal end of the second lumen, the second tubular body also possessing an outer circumference at the distal end of the second tubular body;
- an expandable body fixed to the first tubular body and surrounding an interior space in fluid communication with the first lumen in the first tubular body so that the liquid in the first lumen of the first tubular body flows into the interior space of the expandable body and outwardly expands the expandable body to cause the expandable body to contact an inner surface of the bone surrounding the hole to fix the medical device in position in the hole in the bone; and
- the first lumen possessing a size which gradually decreases from the expandable body toward the distal opening at the distal end of the first lumen so that the liquid introduced into the first lumen by way of the proximal opening at the proximal end of the first lumen and flowing toward the first opening at the distal end of the first lumen enters the interior space of the expandable body and outwardly expands the expandable body into contact with the inner surface of the bone surrounding the hole; and
- wherein the first lumen and the second lumen have mutually independent fluid passages and wherein the outer circumference of the second tubular body at the distal end of the second tubular body is smaller than the inner circumference of the first lumen measured at the distal end of the first lumen so that the liquid in the lumen is dischargeable from the second opening and into the hole in the bone when the second tubular body is positioned at the second opening.

6. The medical device according to claim 5, wherein
- the first lumen possesses a distal-most end positioned at the distal opening of the first lumen;
- the second lumen possesses a distal-most end positioned at the distal opening of the second lumen;
- the distal-most end of the second lumen is configured to axially extend further than the distal-most end of the first lumen, and
- a space exists between an outer circumference of the distal-most end of the second lumen and an inner circumference of the distal-most end of the first lumen when the distal-most end of the second lumen axially extends further than the distal-most end of the first lumen.

7. The medical device according to claim 1, wherein
- the expandable body possesses a distal end fixed to the tubular body and a proximal end fixed to the tubular body, the expandable body being configured to outwardly expand relative to a part of the tubular body immediately adjacent the distal end of the expandable body and to outwardly expand relative to a part of the tubular body immediately adjacent the proximal end of the expandable body.

8. The medical device according to claim 1, wherein
- a wall thickness of the tubular body is substantially uniform from the expandable body to the opening.

9. A medical device positionable in a hole in a bone of a human body, the medical device comprising:
- a first tubular body possessing a size and configuration permitting the first tubular body to be positioned in the hole in the bone of the human body;
- a lumen extending through the first tubular body, the lumen possessing a first opening at one end of the lumen permitting a liquid to be introduced into the lumen and also possessing a second opening at an opposite end of the lumen permitting the liquid in the lumen to be discharged from the lumen and into the hole in the bone, the lumen possessing an inner circumference at the second opening;
- an expandable body fixed to the first tubular body and surrounding an interior space in fluid communication with the lumen in the first tubular body so that the liquid in the lumen of the first tubular body flows into the interior space of the expandable body and outwardly expands the expandable body to cause the expandable body to contact an inner surface of the bone surrounding the hole to fix the medical device in position in the hole in the bone;
- the lumen possessing an inner diameter which gradually decreases from the expandable body to the opening at the opposite end of the lumen such that the inner diameter of the lumen at the opposite end of the lumen is less than the inner diameter of the lumen adjacent to the expandable body so that a portion of the liquid introduced into the lumen by way of the opening at the one end of the lumen and flowing toward the opening at the opposite end of the lumen enters the interior space of the expandable body and outwardly expands the expandable body into contact with the inner surface of the bone surrounding the hole, and another portion of the liquid introduced into the lumen by way of the opening at the one end of the lumen flows to the opposite end of the lumen and is discharged through the opening at the opposite end of the lumen;
- a second tubular body positioned in the lumen and possessing an outer circumference at a distal-most end of the second tubular body; and
- wherein the outer circumference of the second tubular body at the distal-most end of the second tubular body is smaller than the inner circumference of the lumen at the second opening so that the liquid in the lumen is dischargeable from the second opening and into the hole in the bone when the second tubular body is positioned at the second opening.

* * * * *